US009228007B1

(12) United States Patent
Kitchen et al.

(10) Patent No.: US 9,228,007 B1
(45) Date of Patent: Jan. 5, 2016

(54) RECOMBINANT HUMAN PROGENITOR CELLS, ENGINEERED HUMAN THYMOCYTES, AND ENGINEERED HUMAN T CELLS

(75) Inventors: Scott G. Kitchen, Los Angeles, CA (US); Jerome A. Zack, Tarzana, CA (US); Otto O. Yang, Los Angeles, CA (US); Michael S. Bennett, Tucson, AZ (US); Balamurugan Arumugam, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1001 days.

(21) Appl. No.: 13/045,073

(22) Filed: Mar. 10, 2011

Related U.S. Application Data

(60) Provisional application No. 61/312,736, filed on Mar. 11, 2010.

(51) Int. Cl.
*A61K 39/00* (2006.01)
*A61K 45/00* (2006.01)
*A01N 63/00* (2006.01)
*A61K 39/38* (2006.01)
*C12N 5/00* (2006.01)
*C12N 5/02* (2006.01)
*C07K 14/725* (2006.01)

(52) U.S. Cl.
CPC .................................. *C07K 14/7051* (2013.01)

(58) Field of Classification Search
CPC . C12Q 1/68; G01N 33/5008; G01N 33/5091; A61K 39/3955
USPC ........................................................ 424/85.2
See application file for complete search history.

(56) References Cited

U.S. PATENT DOCUMENTS

2005/0009180 A1* 1/2005 Yang et al. .................... 435/455
2009/0217403 A1* 8/2009 Spits ............................... 800/18

FOREIGN PATENT DOCUMENTS

WO 2008127670 A1 10/2008

OTHER PUBLICATIONS

Yang et al., 2005, PNAS (USA) 102:4518-4523.*
Uko et al (2001, Genes and immunity 2:11-19.*
USPTO sequence search Run on Apr. 20, 2015 pp. 1-2.*
Agarwal, M. et al. (1997) "Scaffold Attachment Region-Mediated Enhancement of Retroviral Vector Expression in Primary T Cells" J Virol.. 72(5): 3720-3728.
Bendle, G. (2009) "Preclinical Development of T Cell Receptor Gene Therapy" Current Op. in Immunology 23: 209-214.
Berry, L.J. (2009) "Adoptive Immunotherapy for cancer: the Next Generation of Gene-Engineered Immune Cells" Tissue Antigens, 74:277-289.
Clay, T. (1998) "Potential Use of T Cell Receptor Genes to Modify Hematopoietic Stem Cells for the Gener Therapy fo Cancer" Pathology Oncology Research, 5(1).
Cohen, J. (2007) "Building an HIV-Proof Immune System" Science, 317: 612-614.
Fleming, H. et al. (2006) "Embryonic Stem Cells Make Human T Cells" PNAS, 103(33):12213-12214.
June, C. et al. (2009) "Engineering Lymphocyte Subsets: Tools, Trials, and Tribulations" Nature, 9.
Kitchen, et al. (2009) "Engineering Antigen-Specific T Cells from Genetically Modified Human Hematopoietic Stem Cells in Immunodeficient Mice" PLoSONE, 4(12):1-9.
Maim-Chouaib, Fathia (2002) "Antitumor Cytotoxic T-lymphocyte Response in Human Lung Carcinoma: Identification of a Tumor-associated Antigen" Immunological Reviews,188: 114-121.
Mitsuyasu, et al. (2008) "Phase 2 Gene Therapy Trial of an Anti-HIV Ribozyme in Autologous CD34+ Cells" Nature Medicine, 15:285-292.
Norell, et al. (2009) "CD34-based Enrichment of Genetically Engineered Human T Cells for CLinical Use Results in Dramatically Enhanced Tumor Targeting" Cancer Immun. Immunotherapy, 59:851-862.
Rossi, et al. (2007)"Genetic Therapies against HIV" Nature Biotechnology, 25(12):1444-1454.
Schlub, A. et al. (2009) "CMV-specific TCR-transgenic T Cells from Immunotherapy" J. Immunol. 183:6819-6830.
Stauss, H. (2008) "WT1-specific T cell Receptor Gene Therapy: Improving TCR Function in Transduced T cells Blood Cells" Molecules, and Diseases, 40(1):113-116.
Su, L. et al. (1997) "Hematopoietic Stem Cell-based Gene Therapy for Acquired Immunodeficiency Syndrome: Efficient Transduction and Expression of RevM10 in Mycloid Cells in vivo and in vitro" Blood, 1(89):2283-90.
Varela-Rohea, A. et al. (2008) "Control of HIV-1 Immune Escape by CD8 T Cells Expressing Enhanced T-cell Receptor" Nature Medicine, 14:1390-1395.

* cited by examiner

*Primary Examiner* — Scott Long
*Assistant Examiner* — Kelaginamane Hiriyanna
(74) *Attorney, Agent, or Firm* — Suzannah K. Sundby, Esq.; Canady + Lortz LLP

(57) ABSTRACT

Disclosed herein are recombinant human progenitor cells, engineered human thymocytes, and engineered human T cells. The recombinant human progenitor cells are made by transducing a human hematopoietic stem cell with a vector having a nucleic acid molecule which encodes a human T cell receptor specific to a virus, such as Human Immunodeficiency Virus, or an epitope thereof. The recombinant human progenitor cells differentiate and mature into the engineered human thymocytes and the engineered human T cells. Also disclosed herein are methods of inhibiting, reducing or treating a viral infection in a subject, such as a human subject, which comprises administering recombinant human progenitor cells, engineered human thymocytes, and/or engineered human T cells to the subject.

12 Claims, 16 Drawing Sheets

>1.9 (SEQ ID NO:35)

GGATCCGCCACCATGAAATCCTTGAGAGTTTTACTAGTGATCCTGTGGCTTCAGTTGAGCTG
GGTTTGGAGCCAACAGAAGGAGGTGGAGCAGAATTCTGGACCCCTCAGTGTTCCAGAGGGAG
CCATTGCCTCTCTCAACTGCACTTACAGTGACCGAGGTTCCCAGTCCTTCTTCTGGTACAGA
CAATATTCTGGGAAAAGCCCTGAGTTGATAATGTCCATATACTCCAATGGTGACAAAGAAGA
TGGAAGGTTTACAGCACAGCTCAATAAAGCCAGCCAGTATGTTTCTCTGCTCATCAGAGACT
CCCAGCCCAGTGATTCAGCCACCTACCTCTGTGCCGTGATCTCCAATTCAGGAAACACACCT
CTTGTCTTTGGAAAGGGCACAAGACTTTCTGTGATTGCAAATATCCAGAACCCTGACCCTGC
CGTGTACCAGCTGAGAGACTCTAAATCCAGTGACAAGTCTGTCTGCCTATTCACCGATTTTG
ATTCTCAAACAAATGTGTCACAAAGTAAGGATTCTGATGTGTATATCACAGACAAAACTGTG
CTAGACATGAGGTCTATGGACTTCAAGAGCAACAGTGCTGTGGCCTGGAGCAACAAATCTGA
CTTTGCATGTGCAAACGCCTTCAACAACAGCATTATTCCAGAAGACACCTTCTTCCCCAGCC
CAGAAAGTTCCTGTGATGTCAAGCTGGTCGAGAAAAGCTTTGAAACAGATACGAACCTAAAC
TTTCAAAACCTGTCAGTGATTGGGTTCCGAATCCTCCTCCTGAAAGTGGCCGGGTTTAATCT
GCTCATGACGCTGCGGCTGTGGTCCAGCGGTTCCGGAGCCACGAACTTCTCTCTGTTAAAGC
AAGCAGGAGACGTGGAAGAAAACCCCGGTCCCATGGGCTCCAGGCTGCTCTGTTGGGTGCTG
CTTTGTCTCCTGGGAGCAGGCCCAGTAAAGGCTGGAGTCACTCAAACTCCAAGATATCTGAT
CAAAACGAGAGGACAGCAAGTGACACTGAGCTGCTCCCCTATCTCTGGGCATAGGAGTGTAT
CCTGGTACCAACAGACCCCAGGACAGGGCCTTCAGTTCCTCTTTGAATACTTCAGTGAGACA
CAGAGAAACAAAGGAAACTTCCCTGGTCGATTCTCAGGGCGCCAGTTCTCTAACTCTCGCTC
TGAGATGAATGTGAGCACCTTGGAGCTGGGGGACTCGGCCCTTTATCTTTGCGCCAGCAGCT
TTGACTCTGAGCAGTACTTCGGGCCGGGCACCAGGCTCACGGTCACAGAGGACCTGAAAAAC
GTGTTCCCACCCGAGGTCGCTGTGTTTGAGCCATCAGAAGCAGAGATCTCCCACACCCAAAA
GGCCACACTGGTGTGCCTGGCCACAGGCTTCTACCCCGACCACGTGGAGCTGAGCTGGTGGG
TGAATGGGAAGGAGGTGCACAGTGGGGTCAGCACAGACCCGCAGCCCCTCAAGGAGCAGCCC
GCCCTCAATGACTCCAGATACTGCCTGAGCAGCCGCCTGAGGGTCTCGGCCACCTTCTGGCA
GAACCCCCGCAACCACTTCCGCTGTCAAGTCCAGTTCTACGGGCTCTCGGAGAATGACGAGT
GGACCCAGGATAGGGCCAAACCTGTCACCCAGATCGTCAGCGCCGAGGCCTGGGGTAGAGCA
GACTGTGGCTTCACCTCCGAGTCTTACCAGCAAGGGGTCCTGTCTGCCACCATCCTCTATGA
GATCTTGCTAGGGAAGGCCACCTTGTATGCCGTGCTGGTCAGTGCCCTCGTGCTGATGGCCA
TGGTCAAGAGAAAGGATTCCAGAGGCTAGTCTAGA

>1.9 cys (SEQ ID NO:36)

GGATCCGCCACCATGAAATCCTTGAGAGTTTTACTAGTGATCCTGTGGCTTCAGTTGAGCTG
GGTTTGGAGCCAACAGAAGGAGGTGGAGCAGAATTCTGGACCCCTCAGTGTTCCAGAGGGAG
CCATTGCCTCTCTCAACTGCACTTACAGTGACCGAGGTTCCCAGTCCTTCTTCTGGTACAGA
CAATATTCTGGGAAAAGCCCTGAGTTGATAATGTCCATATACTCCAATGGTGACAAAGAAGA
TGGAAGGTTTACAGCACAGCTCAATAAAGCCAGCCAGTATGTTTCTCTGCTCATCAGAGACT
CCCAGCCCAGTGATTCAGCCACCTACCTCTGTGCCGTGATCTCCAATTCAGGAAACACACCT
CTTGTCTTTGGAAAGGGCACAAGACTTTCTGTGATTGCAAATATCCAGAACCCTGACCCTGC
CGTGTACCAGCTGAGAGACTCTAAATCCAGTGACAAGTCTGTCTGCCTATTCACCGATTTTG
ATTCTCAAACAAATGTGTCACAAAGTAAGGATTCTGATGTGTATATCACAGACAAATGTGTG
CTAGACATGAGGTCTATGGACTTCAAGAGCAACAGTGCTGTGGCCTGGAGCAACAAATCTGA
CTTTGCATGTGCAAACGCCTTCAACAACAGCATTATTCCAGAAGACACCTTCTTCCCCAGCC
CAGAAAGTTCCTGTGATGTCAAGCTGGTCGAGAAAAGCTTTGAAACAGATACGAACCTAAAC
TTTCAAAACCTGTCAGTGATTGGGTTCCGAATCCTCCTCCTGAAAGTGGCCGGGTTTAATCT
GCTCATGACGCTGCGGCTGTGGTCCAGCGGTTCCGGAGCCACGAACTTCTCTCTGTTAAAGC
AAGCAGGAGACGTGGAAGAAAACCCCGGTCCCATGGGCTCCAGGCTGCTCTGTTGGGTGCTG
CTTTGTCTCCTGGGAGCAGGCCCAGTAAAGGCTGGAGTCACTCAAACTCCAAGATATCTGAT
CAAAACGAGAGGACAGCAAGTGACACTGAGCTGCTCCCCTATCTCTGGGCATAGGAGTGTAT

Fig. 1

*CCTGGTACCAACAGACCCCAGGACAGGGCCTTCAGTTCCTCTTTGAATACTTCAGTGAGACA*
*CAGAGAAACAAAGGAAACTTCCCTGGTCGATTCTCAGGGCGCCAGTTCTCTAACTCTCGCTC*
*TGAGATGAATGTGAGCACCTTGGAGCTGGGGGACTCGGCCCTTTATCTTTGCGCCAGCAGCT*
*TTGACTCTGAGCAGTACTTCGGGCCGGGCACCAGGCTCACGGTCACAGAG*GACCTGAAAAAC
GTGTTCCCACCCGAGGTCGCTGTGTTTGAGCCATCAGAAGCAGAGATCTCCCACACCCAAAA
GGCCACACTGGTGTGCCTGGCCACAGGCTTCTACCCCGACCACGTGGAGCTGAGCTGGTGGG
TGAATGGGAAGGAGGTGCACAGTGGGGTCTGCACAGACCCGCAGCCCCTCAAGGAGCAGCCC
GCCCTCAATGACTCCAGATACTGCCTGAGCAGCCGCCTGAGGGTCTCGGCCACCTTCTGGCA
GAACCCCCGCAACCACTTCCGCTGTCAAGTCCAGTTCTACGGGCTCTCGGAGAATGACGAGT
GGACCCAGGATAGGGCCAAACCTGTCACCCAGATCGTCAGCGCCGAGGCCTGGGGTAGAGCA
GACTGTGGCTTCACCTCCGAGTCTTACCAGCAAGGGGTCCTGTCTGCCACCATCCTCTATGA
GATCTTGCTAGGGAAGGCCACCTTGTATGCCGTGCTGGTCAGTGCCCTCGTGCTGATGGCCA
TGGTCAAGAGAAAGGATTCCAGAGGCTAGTCTAGA

>codon optimized 1.9 (SEQ ID NO:37)
GGATCCGCCACC*ATGATGAAGAGCCTGCGGGTGCTGCTGGTGATCCTGTGGCTGCAGCTGTC*
*CTGGGTCTGGAGCCAGCAGAAAGAGGTGGAGCAGAACAGCGGCCCTCTGAGCGTGCCCGAGG*
*GCGCCATTGCCAGCCTGAACTGCACCTACAGCGACCGGGGCAGCCAGAGCTTCTTCTGGTAC*
*AGGCAGTACAGCGGCAAGAGCCCCGAGCTGATCATGAGCATCTACAGCAACGGCGACAAAGA*
*GGACGGCCGGTTCACCGCCCAGCTGAACAAGGCCAGCCAGTACGTGTCTCTGCTGATCAGAG*
*ACAGCCAGCCCAGCGACAGCGCCACCTACCTGTGCGCCGTGATCAGCAACAGCGGCAACACC*
*CCCCTGGTGTTCGGCAAGGGCACCAGACTGAGCGTGATCGCCAAC*ATCCAGAACCCCGACCC
CGCCGTGTACCAGCTGCGGGACAGCAAGAGCAGCGACAAGAGCGTGTGCCTGTTCACCGACT
TCGACAGCCAGACCAACGTGAGCCAGAGCAAGGACAGCGACGTGTACATCACCGACAAGACC
GTGCTGGACATGCGGAGCATGGACTTCAAGAGCAACAGCGCCGTGGCCTGGTCCAACAAGAG
CGACTTCGCCTGCGCCAACGCCTTCAACAACAGCATCATCCCCGAGGACACCTTTTTCCCCA
GCCCCGAGAGCAGCTGCGACGTGAAACTGGTGGAGAAGAGCTTCGAGACAGACACCAACCTG
AACTTCCAGAACCTGTCCGTGATCGGCTTCAGAATCCTGCTGCTCAAAGTGGCTGGCTTCAA
CCTGCTGATGACCCTGCGGCTGTGGAGCAGCGGGTCCGGAGCTACCAACTTCAGCCTGCTGA
AGCAGGCCGGCGACGTGGAGGAAAACCCTGGCCCC*ATGGGATCTCGCCTGCTGTGCTGGGTG*
*CTGCTGTGCCTGCTGGGAGCCGGCCCTGTGAAGGCCGGCGTGACCCAGACCCCCAGATACCT*
*GATCAAGACCAGGGGCCAGCAGGTGACCCTGAGCTGCAGCCCCATCAGCGGCCACAGAAGCG*
*TGAGCTGGTATCAGCAGACACCAGGACAGGGCCTGCAGTTCCTGTTCGAGTACTTCAGCGAG*
*ACACAGCGGAACAAGGGCAACTTCCCCGGCAGGTTCAGCGGCAGGCAGTTCAGCAACTCCCG*
*GTCCGAGATGAACGTGAGCACCCTGGAACTGGGCGACTCCGCCCTGTACCTGTGTGCCAGCA*
*GCTTCGACAGCGAGCAGTACTTCGGCCCTGGCACCCGGCTGACCGTGACCGAG*GACCTGAAG
AACGTGTTCCCCCCCGAGGTGGCCGTGTTCGAGCCCAGCGAGGCCGAGATCAGCCACACCCA
GAAAGCCACCCTGGTGTGCCTGGCCACCGGCTTCTACCCCGACCACGTGGAGCTGTCTTGGT
GGGTGAACGGCAAAGAGGTGCACAGCGGAGTCTCCACCGACCCCCAGCCCCTGAAAGAGCAG
CCCGCCCTGAACGACAGCCGGTACTGCCTGAGCAGCAGGCTGAGAGTGAGCGCCACCTTCTG
GCAGAACCCCCGGAACCACTTCCGGTGCCAGGTGCAGTTCTACGGCCTGAGCGAGAACGACG
AGTGGACCCAGGACAGAGCCAAGCCTGTGACCCAGATCGTGTCCGCCGAGGCCTGGGGCAGA
GCCGACTGCGGCTTCACCAGCGAGAGCTATCAGCAGGGAGTGCTGTCTGCCACCATCCTGTA
CGAGATCCTGCTGGGCAAGGCCACCCTGTACGCCGTGCTGGTGTCCGCCCTGGTGCTGATGG
CCATGGTGAAGCGGAAGGACAGCCGGGGCTGATCTAGA >codon optimized 1.9 cys (SEQ ID NO:38)
GGATCCGCCACC*ATGATGAAGAGCCTGCGGGTGCTGCTGGTGATCCTGTGGCTGCAGCTGTC*
*CTGGGTCTGGAGCCAGCAGAAAGAGGTGGAGCAGAACAGCGGCCCTCTGAGCGTGCCCGAGG*
*GCGCCATTGCCAGCCTGAACTGCACCTACAGCGACCGGGGCAGCCAGAGCTTCTTCTGGTAC*

Fig. 1 cont.

*AGGCAGTACAGCGGCAAGAGCCCCGAGCTGATCATGAGCATCTACAGCAACGGCGACAAAGA*
*GGACGGCCGGTTCACCGCCCAGCTGAACAAGGCCAGCCAGTACGTGTCTCTGCTGATCAGAG*
*ACAGCCAGCCCAGCGACAGCGCCACCTACCTGTGCGCCGTGATCAGCAACAGCGGCAACACC*
*CCCCTGGTGTTCGGCAAGGGCACCAGACTGAGCGTGATCGCCAAC*ATCCAGAACCCCGACCC
CGCCGTGTACCAGCTGCGGGACAGCAAGAGCAGCGACAAGAGCGTGTGCCTGTTCACCGACT
TCGACAGCCAGACCAACGTGAGCCAGAGCAAGGACAGCGACGTGTACATCACCGACAAGTGC
GTGCTGGACATGCGGAGCATGGACTTCAAGAGCAACAGCGCCGTGGCCTGGTCCAACAAGAG
CGACTTCGCCTGCGCCAACGCCTTCAACAACAGCATCATCCCCGAGGACACCTTTTTCCCCA
GCCCCGAGAGCAGCTGCGACGTGAAACTGGTGGAGAAGAGCTTCGAGACAGACACCAACCTG
AACTTCCAGAACCTGTCCGTGATCGGCTTCAGAATCCTGCTGCTCAAAGTGGCTGGCTTCAA
CCTGCTGATGACCCTGCGGCTGTGGAGCAGCGGGTCCGGAGCTACCAACTTCAGCCTGCTGA
AGCAGGCCGGCGACGTGGAGGAAAACCCTGGCCCC*ATGGGATCTCGCCTGCTGTGCTGGGTG*
*CTGCTGTGCCTGCTGGGAGCCGGCCCTGTGAAGGCCGGCGTGACCCAGACCCCCAGATACCT*
*GATCAAGACCAGGGGCCAGCAGGTGACCCTGAGCTGCAGCCCCATCAGCGGCCACAGAAGCG*
*TGAGCTGGTATCAGCAGACACCAGGACAGGGCCTGCAGTTCCTGTTCGAGTACTTCAGCGAG*
*ACACAGCGGAACAAGGGCAACTTCCCCGGCAGGTTCAGCGGCAGGCAGTTCAGCAACTCCCG*
*GTCCGAGATGAACGTGAGCACCCTGGAACTGGGCGACTCCGCCCTGTACCTGTGTGCCAGCA*
*GCTTCGACAGCGAGCAGTACTTCGGCCCTGGCACCCGGCTGACCGTGACCGAG*GACCTGAAG
AACGTGTTCCCCCCCGAGGTGGCCGTGTTCGAGCCCAGCGAGGCCGAGATCAGCCACACCCA
GAAAGCCACCCTGGTGTGCCTGGCCACCGGCTTCTACCCCGACCACGTGGAGCTGTCTTGGT
GGGTGAACGGCAAAGAGGTGCACAGCGGAGTCTGCACCGACCCCCAGCCCCTGAAAGAGCAG
CCCGCCCTGAACGACAGCCGGTACTGCCTGAGCAGCAGGCTGAGAGTGAGCGCCACCTTCTG
GCAGAACCCCCGGAACCACTTCCGGTGCCAGGTGCAGTTCTACGGCCTGAGCGAGAACGACG
AGTGGACCCAGGACAGAGCCAAGCCTGTGACCCAGATCGTGTCCGCCGAGGCCTGGGGCAGA
GCCGACTGCGGCTTCACCAGCGAGAGCTATCAGCAGGGAGTGCTGTCTGCCACCATCCTGTA
CGAGATCCTGCTGGGCAAGGCCACCCTGTACGCCGTGCTGGTGTCCGCCCTGGTGCTGATGG
CCATGGTGAAGCGGAAGGACAGCCGGGGCTGATCTAGA

*Italics* = variable region
Highlight = Constant region
Bold = Self-cleaving 2A peptide
Double underline = restriction sites
Underline = stop codon
Bold underline = Cysteine mutation

Fig. 1 cont.

COMPARISON OF METHODOLOGIES TO ISOLATE EPITOPE-SPECIFIC TCR
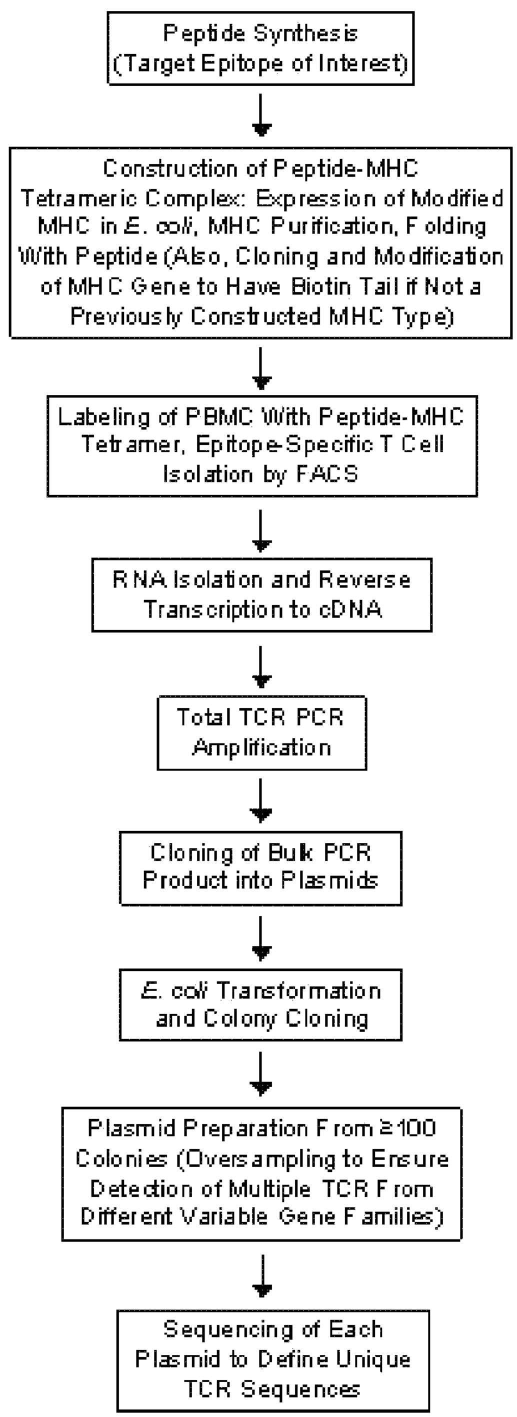
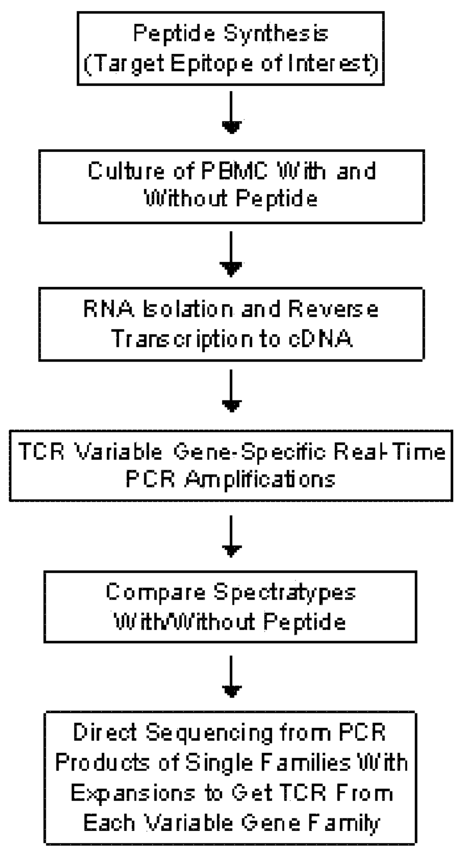
Fig. 4

RECOMBINANT HUMAN PROGENITOR CELLS, ENGINEERED HUMAN THYMOCYTES, AND ENGINEERED HUMAN T CELLS

CROSS-REFERENCE TO RELATED APPLICATIONS

This application claims the benefit of U.S. Patent Application Ser. No. 61/312,736, filed 11 Mar. 2010, which is herein incorporated by reference in its entirety.

REFERENCE TO A SEQUENCE LISTING SUBMITTED VIA EFS-WEB

The content of the ASCII text file of the sequence listing named "20110309_034044_073_ST25" which is 80.7 kb in size was created on 9 Mar. 2011 and electronically submitted via EFS-Web herewith the application is incorporated herein by reference in its entirety.

THE BACKGROUND OF THE INVENTION

1. Field of the Invention

The present invention generally relates to recombinant human progenitor cells, engineered human thymocytes, and engineered human T cells, and methods of treating subjects therewith.

2. Description of the Related Art

There are currently no known therapeutic cures for a variety of chronic viral infections. Many viruses, including human immunodeficiency virus (HIV), hepatitis B virus (HBV), hepatitis C virus (HCV), various herpes family viruses (herpes simplex virus type 1 and 2, Varicella-Zoster virus, Epstein-Bar virus, etc), human papillomavirus, and many others establish a persistent, often lifelong infection with the host organism. Such chronic viral infections are often accompanied with significant morbidity and a lower quality of life. The persistence of these chronic viral infections is due in part to the inability of the human immune system to adequately control and ultimately clear the virus from the body and the lack of effective therapies and medicines that can clear the virus from the body.

In many of these viral infections, the cytotoxic T lymphocyte (CTL) response is important in controlling viral replication and the failure of this response may significantly contribute to the inability of the body to fully control or clear the virus. See Berzofsky, et al. (2004) J Clin Invest. 114(4): 450-462. For example, the CD8+ T cell CTL response plays an important role in controlling the amount of Human Immunodeficiency Virus type 1 (HIV-1) in the body of an infected individual. See Benito, et al. (2004) AIDS Rev. 6(2): 79-88; Borrow, et al. (1994) J Virol. 68(9): 6103-6110; and Rowland-Jones, et al. (2001) Immunol Lett. 79(1-2): 15-20. CTLs specific for various HIV-1 antigenic epitopes are primarily responsible for the initial control and lowering of the viral load in the body shortly after infection with HIV and are responsible for controlling viral loads throughout infection. See Koup, et al. (1994) J Virol. 68(7): 4650-4655. Inevitably, the CTL response in HIV infected individuals fails during the natural course of infection. The loss of the HIV-specific immune response, particularly the CTL response, is associated with an increase in the HIV viral load and a more rapid progression to AIDS and death. See Goulder, et al. (1997) Nat Med. 3(2): 212-217; and Huynen & Neumann (1986) Science. 272(5270): 1962. The virus itself, placed under selective pressure by the CTL response, mutates to avoid the CTL response. See Wolinsky, et al. (1996) Science. 272(5261): 537-542. This results in the virus escaping immune surveillance and is usually followed by the generation of new CTLs to different antigenic epitopes.

One method of augmenting CTL responses is to generate homologous antigen-specific CTLs ex vivo and then administer the ex vivo generated cells into the subject to be treated. This treatment has been effective for treating cytomegalovirus (CMV) and Epstein-Barr virus (EBV) chronic infections, however, this treatment has not been shown to be effective in treating HIV infected individuals. See Lieberman, et al. (1997) Blood. 90(6): 2196-2206; Brodie, et al. (1999) Nat Med. 5(1): 34-41; Bollard, et al. (2004) Biol Blood Marrow Transplant. 10(3): 143-55; and Joseph, et al. (2008) J Virol. 82(6): 3078-3089. In HIV infected individuals, the ex vivo generated CTLs are likely to be dysfunctional as the autologous CTLs are ineffective at clearing or controlling the viral infection as a direct result of the HIV infection and ongoing viral-induced pathology.

Several studies have demonstrated the ability of cloned, antigen specific TCR α-chains and β-chains to be genetically transferred into autologous, stimulated CD8+ T lymphocytes and generate antigen-specific cells. See Hughes, et al. (2005) Hum Gene Ther. 16(4): 457-472; Johnson, et al. (2006) J Immunol. 177(9): 6548-6559; Miles, et al. (2006) Curr Med Chem. 13(23): 2725-2736; and Morgan, et al. (2006) Science. 314(5796): 126-129. Genetic transfer of a cloned human TCR to the melanoma antigen MART-1 into autologous CD8+ T lymphocytes followed by re-infusion of the cells into cancer patients with metastatic melanoma resulted in tumor cell regression in treated individuals. Unfortunately, these autologous cells taken from the treated patient have to undergo extensive ex vivo manipulation to express the transgenic TCR following re-infusion, which could at least partially explain the large amount of MART-1 TCR specific cells that were functionally deficient in this study. In addition, while the cells in this study were maintained for a relatively long period of time, long-term regeneration of antigen-specific cells was limited and the methodology of the study does not allow the generation of antigen-specific cells of a "naïve", or non-exhausted or unmanipulated, phenotype and thus lack the robust ability to respond and function.

With all the advances in stem cell technology today, the prior art has yet to provide recombinant human progenitor cells, engineered human thymocytes (which may be naïve cells), and engineered human T cells which express a human TCR specific for a target antigen, such as an HIV antigen, that may be used to effectively treat a human subject against a disease or infection involving the expression of the target antigen. Thus, a need still exists for such compositions and methods, especially for treating chronic viral infections where the virus inhibits or impairs the native CTL response.

SUMMARY OF THE INVENTION

In some embodiments, the present invention provides a recombinant human progenitor cell which comprises a hematopoietic stem cell transduced with a vector containing a nucleic acid molecule which encodes a T cell receptor specific for a virus or an epitope thereof. In some embodiments, the epitope comprises, consists essentially of, or consists of SEQ ID NO:1; SEQ ID NO:2; SEQ ID NO:3; SEQ ID NO:4; SEQ ID NO:5; or SEQ ID NO:6. In some embodiments, the hematopoietic stem cell, the nucleic acid molecule, and/or the T cell receptor is human or of human origin. In some embodiments, the T cell receptor is a functional T cell receptor when expressed. In some embodiments, the nucleic acid molecule encodes a according to the present invention. In some embodiments, the virus is a human immunodeficiency virus, such as HIV-1, or Orthomyxoviruses, such as Influenza virus. In some embodiments, the T cell receptor was cloned by a spectratyping-based cloning method. In some embodiments, the vector is pCCL.PPT.hPGK.tcr.IRES.eGFP vector, wherein the TCR segment encodes the T cell receptor.

In some embodiments, the present invention provides an isolated or purified polypeptide a polypeptide comprising, consisting essentially of, or consisting of a first sequence having a 90%, 91%, 92%, 93%, 94%, 95%, 96%, 97%, 98%, 99%, or 100% identity to SEQ ID NO:7 and a second sequence having a 90%, 91%, 92%, 93%, 94%, 95%, 96%, 97%, 98%, 99%, or 100% identity to SEQ ID NO:8; a first sequence having a 90%, 91%, 92%, 93%, 94%, 95%, 96%, 97%, 98%, 99%, or 100% identity to SEQ ID NO:9 and a second sequence having a 90%, 91%, 92%, 93%, 94%, 95%, 96%, 97%, 98%, 99%, or 100% identity to SEQ ID NO:10; a first sequence having a 90%, 91%, 92%, 93%, 94%, 95%, 96%, 97%, 98%, 99%, or 100% identity to SEQ ID NO:11 or SEQ ID NO:12 and a second sequence having a 90%, 91%, 92%, 93%, 94%, 95%, 96%, 97%, 98%, 99%, or 100% identity to SEQ ID NO:13; a first sequence having a 90%, 91%, 92%, 93%, 94%, 95%, 96%, 97%, 98%, 99%, or 100% identity to SEQ ID NO:14 and a second sequence having a 90%, 91%, 92%, 93%, 94%, 95%, 96%, 97%, 98%, 99%, or 100% identity to SEQ ID NO:15 or SEQ ID NO:16; a first sequence having a 90%, 91%, 92%, 93%, 94%, 95%, 96%, 97%, 98%, 99%, or 100% identity to SEQ ID NO:17 and a second sequence having a 90%, 91%, 92%, 93%, 94%, 95%, 96%, 97%, 98%, 99%, or 100% identity to SEQ ID NO:18; a first sequence having a 90%, 91%, 92%, 93%, 94%, 95%, 96%, 97%, 98%, 99%, or 100% identity to SEQ ID NO:19 and a second sequence having a 90%, 91%, 92%, 93%, 94%, 95%, 96%, 97%, 98%, 99%, or 100% identity to SEQ ID NO:20; a first sequence having a 90%, 91%, 92%, 93%, 94%, 95%, 96%, 97%, 98%, 99%, or 100% identity to SEQ ID NO:21 and a second sequence having a 90%, 91%, 92%, 93%, 94%, 95%, 96%, 97%, 98%, 99%, or 100% identity to SEQ ID NO:22; a first sequence having a 90%, 91%, 92%, 93%, 94%, 95%, 96%, 97%, 98%, 99%, or 100% identity to SEQ ID NO:23 and a second sequence having a 90%, 91%, 92%, 93%, 94%, 95%, 96%, 97%, 98%, 99%, or 100% identity to SEQ ID NO:24; a first sequence having a 90%, 91%, 92%, 93%, 94%, 95%, 96%, 97%, 98%, 99%, or 100% identity to SEQ ID NO:25 or SEQ ID NO:26 and a second sequence having a 90%, 91%, 92%, 93%, 94%, 95%, 96%, 97%, 98%, 99%, or 100% identity to SEQ ID NO:27; or a first sequence having a 90%, 91%, 92%, 93%, 94%, 95%, 96%, 97%, 98%, 99%, or 100% identity to SEQ ID NO:28; SEQ ID NO:29; or SEQ ID NO:30 and a second sequence having a 90%, 91%, 92%, 93%, 94%, 95%, 96%, 97%, 98%, 99%, or 100% identity to SEQ ID NO:31; SEQ ID NO:32; SEQ ID NO:33; or SEQ ID NO:34.

In some embodiments, the present invention provides an isolated or purified nucleic acid molecule which encodes a polypeptide comprising, consisting essentially of, or consisting of a first sequence having a 90%, 91%, 92%, 93%, 94%, 95%, 96%, 97%, 98%, 99%, or 100% identity to SEQ ID NO:7 and a second sequence having a 90%, 91%, 92%, 93%, 94%, 95%, 96%, 97%, 98%, 99%, or 100% identity to SEQ ID NO:8; a first sequence having a 90%, 91%, 92%, 93%, 94%, 95%, 96%, 97%, 98%, 99%, or 100% identity to SEQ ID NO:9 and a second sequence having a 90%, 91%, 92%, 93%, 94%, 95%, 96%, 97%, 98%, 99%, or 100% identity to SEQ ID NO:10; a first sequence having a 90%, 91%, 92%, 93%, 94%, 95%, 96%, 97%, 98%, 99%, or 100% identity to SEQ ID NO:11 or SEQ ID NO:12 and a second sequence having a 90%, 91%, 92%, 93%, 94%, 95%, 96%, 97%, 98%, 99%, or 100% identity to SEQ ID NO:13; a first sequence having a 90%, 91%, 92%, 93%, 94%, 95%, 96%, 97%, 98%, 99%, or 100% identity to SEQ ID NO:14 and a second sequence having a 90%, 91%, 92%, 93%, 94%, 95%, 96%, 97%, 98%, 99%, or 100% identity to SEQ ID NO:15 or SEQ ID NO:16; a first sequence having a 90%, 91%, 92%, 93%, 94%, 95%, 96%, 97%, 98%, 99%, or 100% identity to SEQ ID NO:17 and a second sequence having a 90%, 91%, 92%, 93%, 94%, 95%, 96%, 97%, 98%, 99%, or 100% identity to SEQ ID NO:18; a first sequence having a 90%, 91%, 92%, 93%, 94%, 95%, 96%, 97%, 98%, 99%, or 100% identity to SEQ ID NO:19 and a second sequence having a 90%, 91%, 92%, 93%, 94%, 95%, 96%, 97%, 98%, 99%, or 100% identity to SEQ ID NO:20; a first sequence having a 90%, 91%, 92%, 93%, 94%, 95%, 96%, 97%, 98%, 99%, or 100% identity to SEQ ID NO:21 and a second sequence having a 90%, 91%, 92%, 93%, 94%, 95%, 96%, 97%, 98%, 99%, or 100% identity to SEQ ID NO:22; a first sequence having a 90%, 91%, 92%, 93%, 94%, 95%, 96%, 97%, 98%, 99%, or 100% identity to SEQ ID NO:23 and a second sequence having a 90%, 91%, 92%, 93%, 94%, 95%, 96%, 97%, 98%, 99%, or 100% identity to SEQ ID NO:24; a first sequence having a 90%, 91%, 92%, 93%, 94%, 95%, 96%, 97%, 98%, 99%, or 100% identity to SEQ ID NO:25 or SEQ ID NO:26 and a second sequence having a 90%, 91%, 92%, 93%, 94%, 95%, 96%, 97%, 98%, 99%, or 100% identity to SEQ ID NO:27; or a first sequence having a 90%, 91%, 92%, 93%, 94%, 95%, 96%, 97%, 98%, 99%, or 100% identity to SEQ ID NO:28; SEQ ID NO:29; or SEQ ID NO:30 and a second sequence having a 90%, 91%, 92%, 93%, 94%, 95%, 96%, 97%, 98%, 99%, or 100% identity to SEQ ID NO:31; SEQ ID NO:32; SEQ ID NO:33; or SEQ ID NO:34.

In some embodiments, the present invention provides a recombinant cell and/or a vector which comprises one or more nucleic acid molecules according to the present invention.

In some embodiments, the present invention provides a method of producing an engineered human thymocyte or an engineered human T cell which comprises differentiating a genetically modified human progenitor cell as disclosed herein into the engineered human thymocyte, and maturing the engineered human thymocyte into the engineered human T cell. In some embodiments, the recombinant human progenitor cell is subjected to a thymus tissue which may be human thymus tissue. In some embodiments, the recombinant human progenitor cell is implanted in the thymus tissue of a subject or intravenously administered to the subject. In some embodiments, the engineered human T cell is activated by subjecting it to an HLA molecule specific for the T cell receptor. In some embodiments, the HLA molecule is HLA-A*0201.

In some embodiments, the present invention provides an engineered human thymocyte and/or an engineered human T cell made by the methods disclosed herein. In some embodiments, the engineered human thymocyte and/or the engineered human T cell express a functional T cell receptor, preferably a functional human T cell receptor. In some embodiments, the human T cell receptor is functional in vivo. In some embodiments, the engineered human T cell is a cytotoxic T cell.

In some embodiments, the present invention provides a method of inhibiting, reducing or treating a viral infection in a subject which comprises administering a recombinant human progenitor cell, an engineered human thymocyte and/or an engineered human T cell as described herein to the subject. In some embodiments, the hematopoietic stem cell, the nucleic acid molecule, the thymus tissue, or a combination thereof is obtained from the subject to be treated. In some embodiments, the hematopoietic stem cell, the nucleic acid molecule, the thymus tissue, or a combination thereof is obtained from a donor who is immunologically compatible with the subject to be treated. In some embodiments, the subject to be treated is determined to be in need thereof as the subject has the viral infection, has been exposed to the virus, or will be exposed to the virus.

In some embodiments, the present invention provides kits which comprise a recombinant human progenitor cell, an engineered human thymocyte and/or an engineered human T cell as described herein packaged together with a reagent and/or a device for administering the recombinant human progenitor cell, the engineered human thymocyte and/or the engineered human T cell to a subject.

In the embodiments disclosed herein, the subject is mammalian, preferably human.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1 provides the nucleic acid sequence for the HIV specific human TCR. The 1.9 sequence (SEQ ID NO:35) is the original sequence of the cloned TCR specific for the SL9 epitope from an infected individual. The 1.9 cys sequence (SEQ ID NO:36) is the original 1.9 sequence having modifications which introduce cysteine residues in the constant region to allow greater pairing of the alpha and beta chains. The codon optimized 1.9 sequence (SEQ ID NO:37) is the original 1.9 sequence with several codon modifications to allow greater expression in genetically modified cells. The codon optimized 1.9 cys sequence (SEQ ID NO:38) is the original 1.9 sequence having modifications which introduce cysteine residues in the constant region to allow for greater pairing of the alpha and beta chains and several codon modifications to allow for greater expression in genetically modified cells.

FIG. 4 shows a comparison of the spectratyping-based TCR cloning strategy to a prior art cloning strategy.

DETAILED DESCRIPTION OF THE INVENTION

Figure 2A:
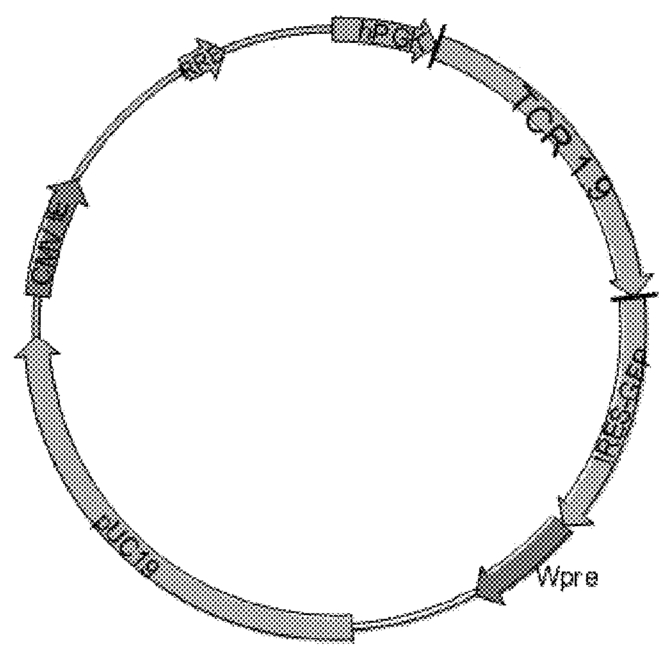
FIG. 2A schematically shows the pCCL.PPT.hPGK.tcr1.9.IRES.eGFP.Wpre vector exemplified herein. The backbone of this vector is described by Dull et al. (1998) J Virol. 72(11): 8463-8471, which is herein incorporated by reference in its entirety.

The present invention provides recombinant human progenitor cells, engineered human thymocytes, and engineered human antigen specific T cells, including cytotoxic T cells (CTLs), which are functional in vivo, and methods of making thereof. The recombinant progenitor cells are genetically engineered from human stem cells, preferably human hematopoietic stem cells, and result in the engineered human thymocytes and/or the engineered human T cells of the present invention.

The engineered human thymocytes and engineered human T cells express anti-viral specific human T cell receptors (TCRs) and are functional in vivo. As used herein, the term "T cell receptor" includes a complex of polypeptides comprising at least a T cell receptor α subunit and a T cell receptor β subunit. T cell receptors (TCRs) are able to bind a given antigen when expressed on the surface of a cell, such as a T lymphocyte. The α and β chains, or subunits, form a dimer that is independently capable of antigen binding. The α and β subunits typically comprise a constant domain and a variable domain and may be native, full-length polypeptides, or may be modified in some way, provided that the T cell receptor retains the ability to bind the given antigen. The complementarity-determining regions (CDR) of the α and β subunits are the antigen binding domain loops and are regions of sequence hypervariability. The specific sequences/structures in this region of a given TCR provides the ability of the TCR to recognize a specific antigen. In the context of a specific HLA molecule.

In some embodiments, the engineered human thymocytes and/or engineered human T cells express functional human TCRs which are functional in vivo. As used herein, a "functional TCR" is one that binds the specific antigen to which it is directed as determined by, for example, using an ELISA assay and/or mediates an immune response against the specific antigen. For example, a "functional HIV TCR" is one that binds an HIV antigen and/or mediates an immune response against HIV. In some embodiments of the present invention, the recombinant human progenitor cells, the engineered human thymocytes, and/or the engineered human T cells are functional in human subjects (as determined from tests in human subjects and/or human animal models). As used herein, a "receptor specific for" refers to the character of a receptor which recognizes and interacts with a given ligand, e.g. target antigen, but does not substantially recognize and interact with other molecules in a sample under given conditions.

The recombinant human progenitor cells, the engineered human thymocytes, and/or the engineered human T cells of the present invention may be used to reconstitute immune function and control replication of a virus, such as human immunodeficiency virus (HIV), in subjects, e.g. human subjects. Therefore, the present invention also provides methods of inhibiting, reducing and treating viral infections, such as an HIV infection, in a subject, such as a human subject. The treatment method according to the present invention may be therapeutic or prophylactic and need not completely eliminate the infection or completely prevent a subject from becoming infected. The present invention also provides methods for enhancing the antigen specific CTL response against a chronic viral infection, such as an HIV infection, in a subject, such as a human subject.

The methods of the present invention provide naïve human cells bearing a transgenic human TCR that is antigen specific, e.g. antigen specific CD8+ CTLs, that allow longer-term engraftment, continuous generation of new effector cells and a more efficient immune response through natural immune mechanisms in human subjects and/or humanized animal models as compared to genetic modification of mature, peripheral blood mononuclear cells.

Some of the human TCR clones, recombinant human progenitor cells, the engineered human thymocytes, the engineered human T cells, and methods of making and using thereof as disclosed herein are also described in the journal article by the inventors, i.e. Kitchen et al. (2009) PLoS ONE 4(12):e8208, all of which is herein incorporated by reference in its entirety.

Unlike prior art efforts which merely differentiate transgenic CTLs in vitro, the present invention provides recombinant human progenitor cells and engineered human naïve thymocytes which are capable of developing in vivo in human thymus tissue and mature into functional CD8+ T cells.

TCR Cloning

The present invention also provides methods of making the recombinant human progenitor cells, engineered human thymocytes, and engineered human T cells of the present invention. Generally, the recombinant human progenitor cells are made from human stem cells, preferably hematopoietic stem cells, by transducing the stem cells with a vector which is capable of expressing a TCR of interest. Briefly, the TCR specific for a virus of interest, e.g. HIV, or an immunogenic epitope thereof, e.g. SL9, is cloned and then the human stem cell is transduced with a vector containing the TCR clone to give the recombinant human progenitor cell. The recombinant human progenitor cell is allowed to develop into an engineered human thymocyte which then matures into the corresponding engineered human T cell, i.e. a functional human T cell which expresses the cloned T cell receptor. In some embodiments, the engineered human T cell is a CTL.

The TCR of interest may be cloned from a pool of samples obtained from a plurality of subjects infected with the given virus to obtain a "consensus" TCR clone. Alternatively, the TCR of interest may be cloned from a sample obtained from the subject to be treated in order to obtain a "personalized" TCR clone for providing the subject with a personalized therapeutic treatment. Methods known in the art may be used to obtain a consensus TCR clone and/or a personalized TCR clone.

For example, peripheral blood mononuclear cells (PBMCs) are removed from a subject having a viral infection, such as an HIV infection. Part of the PBMCs is then cultured with the antigen, i.e. the virus of interest or the immunogenic epitope thereof, and the other part of the PMBCs is cultured without the antigen. Fingerprints which break down all TCRs into over 200 populations for each of the TCR α- and β-genes are obtained for the PBMCs cultured with the antigen and the PMBCs cultured without the antigen by spectratyping. The differences between the fingerprints indicate the TCR sequences of interest. Then the TCR sequences of interest are cloned using methods known in the art.

The TCR clone, as exemplified herein, was isolated from an HIV-positive subject via peptide stimulation and limiting dilution. In particular, PBMCs were obtained from a HLA-A*0201+, HIV infected individual. Part of the PBMCs were cultured with allogeneic, irradiated PBMCs from a different HIV− donor and part of the PBMCs were cultured with a HLA-A*0201+ cell line pretreated with the epitope of interest, i.e. SL9. The cell cultures were fed with fresh medium every 3 to 4 days, and were split and placed on fresh, irradiated PBMCs once every 10 to 14 days.

Spectratyping was used to identify and isolate the TCR sequences specific for the SL9 epitope using methods known in the art. See Balamurugan, et al. (2010) J Immunol. 185(10): 5935-5942; and Frohman (1994) PCR Methods Appl. 4(1): S40-S58, which are herein incorporated by reference. Specifically, the TCR specific for the SL9 epitope was identified following isolation of total RNA, reverse transcription of total cDNA, and quantitative PCR using primers specific to each TCR family to determine the relative concentration of each family. Capillary electrophoresis was then performed, the size distribution of DNA fragments amplified within each TCR family was resolved, and individual peak concentrations were calculated. A comparison was made between the antigen stimulated and unstimulated cells and differences between the spectratypes of the TCR families were noted. The PCR reaction products of the TCRs that displayed differences following antigen stimulation were then directly sequenced.

Figure 2B:
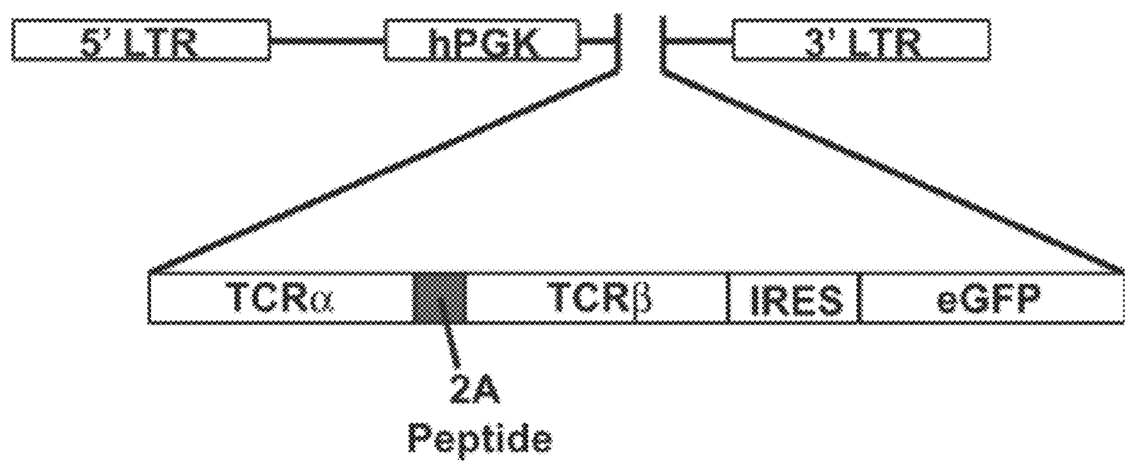
FIG. 2B shows a detail of the lentiviral vector contained in the pCCL.PPT.hPGK.tcr1.9.IRES.eGFP.Wpre plasmid.

The TCR sequences were then synthesized and molecularly cloned into a vector, preferably a viral gene therapy vector. Specifically, the cloned TCRα and TCRβ nucleotide sequences were then joined by a sequence encoding picornavirus-like 2A "self-cleaving" peptide. See Yang, et al. (2008) Gene Ther. 15(21): 1411-1423, which is herein incorporated by reference. FIG. 1 sets forth the exemplified TCR sequence of interest, i.e. 1.9 TCR. The short 18 amino acid 2A sequence which separates the TCRα and TCRβ results in equimolar expression of the TCRα and TCRβ via a "ribosomal skip" mechanism. See Szymczak, et al. (2004) Nat Biotechnol. 22(5): 589-594; and Szymczak & Vignali (2005) Expert Opin Biol Ther. 5(5): 627-638, which are herein incorporated by reference. The TCRα-2A-TCRβ nucleotide sequence was cloned into a lentiviral vector under control of the human phosphoglycerate kinase promoter (hPGK), followed by an internal ribosomal elongation site (IRES) which allows further enhancement of expression of a marker gene, i.e. enhanced green fluorescent protein (eGFP). IRES elements and 2A elements are known in the art. See U.S. Pat. No. 4,937,190; de Felipe, et al. (2004) Traffic 5: 616-626, which are incorporated herein by reference. Other expression control elements, viral vectors, and reporter genes known in the art may be used to further enhance or direct expression of the TCR to various cell types. See e.g. US 20080199424, which is herein incorporated by reference. As exemplified herein, the vector employed is the lentiviral pCCL.PPT.hPGK.tcr.IRES.eGFP vector. FIG. 2 schematically shows the vector containing the 1.9 TCR sequence.

SL9-specificity of the cloned TCR was confirmed by transfecting Jurkat cells with the lentiviral vector containing the TCRα-2A-TCRβ construct and staining with SL9 tetramer using methods known in the art. The lentiviral vector containing the TCRα-2A-TCRβ construct was then codon optimized for optimal expression in human cells using methods known in the art. See Scholten, et al. (2006) Clin Immunol. 119(2):

135-145, which is herein incorporated by reference. The cloned TCR of the codon optimized vector was also shown to retain SL9 specificity by transfecting Jurkat cells with the codon optimized vector containing the TCRα-2A-TCRβ construct and staining with SL9 tetramer using methods known in the art.

Figure 3:
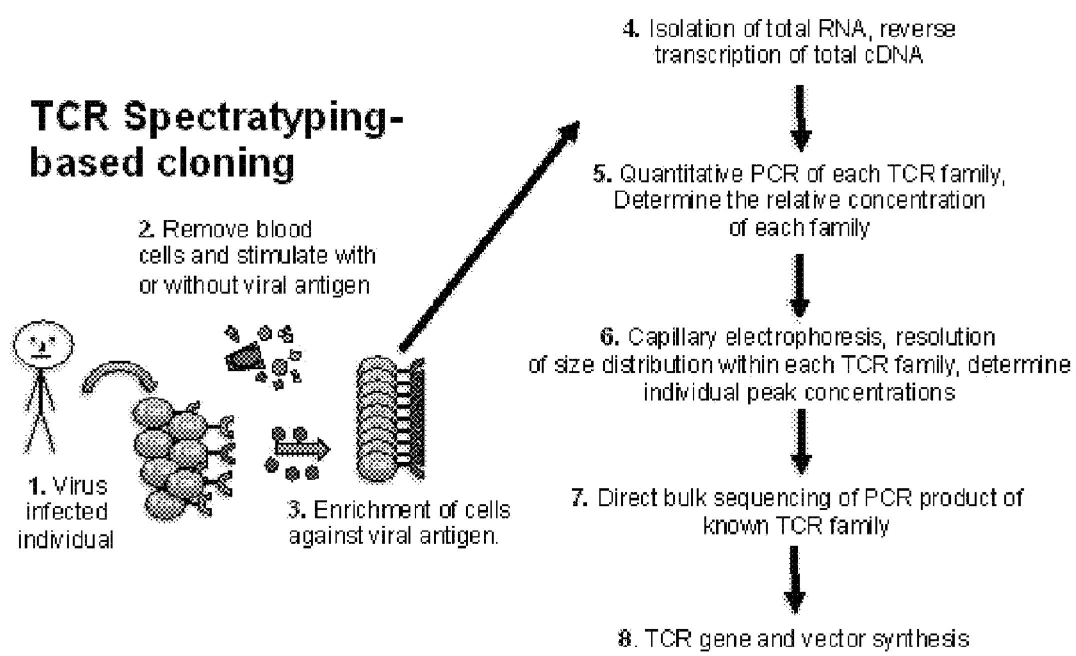
FIG. 3 schematically shows the spectratyping-based TCR cloning strategy according to the present invention.

FIG. 3 schematically shows the TCR spectratyping-based cloning as exemplified herein and FIG. 4 compares this TCR spectratyping-based cloning with a conventional method known in the art.

The methods and vectors according to the present invention may be readily modified using methods known in the art to include clinically relevant reporters or selection markers that may be used to identify and/or isolate successfully transduced stem cells. For example, a recombinant progenitor cell could be engineered to express a receptor, such as a truncated human nerve growth factor receptor, on its surface. Preferably, the receptor would not have signaling properties that would have a detrimental effect on the desired function of the progenitor cell. Preferably, the receptor does not induce an immunogenic response in the subject to be treated. The receptor could then be used to sort or select recombinant progenitor cells prior to their introduction into a subject.

Figure 5A:
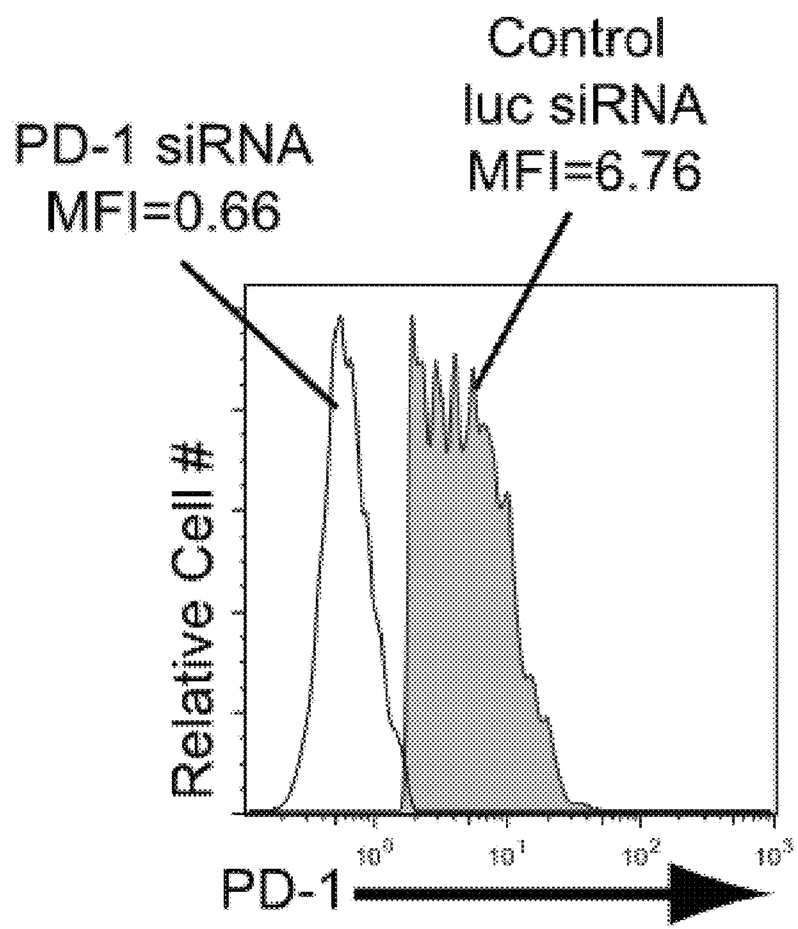
FIG. 5A provides the results which demonstrate that molecules, in this case siRNA, which can interact with cellular molecules to alter or enhance cellular function, can be introduced into and included in the TCR-containing vector.
Figure 5B:
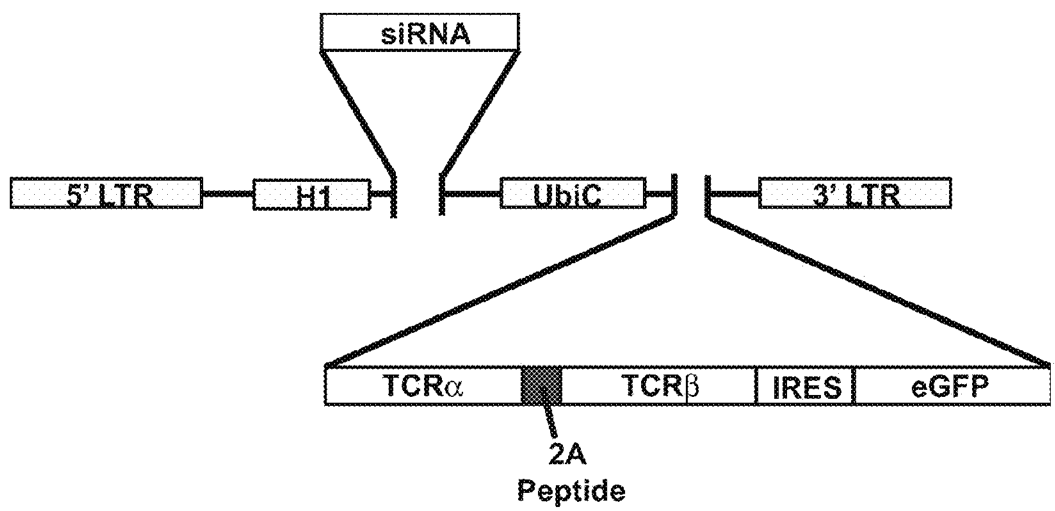
FIG. 5B schematically shows the construct having the siRNA inserted therein.

The cloned TCRs can be combined with small interfering (si), or short hairpin (sh) RNAs against molecules that modulate T cell development and T cell function to modify the activity of the cell expressing the transgenic TCR. For example, a siRNA specific against the Programmed Death-1 (PD-1) gene was designed and cloned into the gene therapy vector that also expresses the SL-9 specific TCR. See FIG. 5. Programmed Death-1 (PD-1) is associated with decreased development and deceased function of antigen-specific T cells. See Simone, et al. (2009) Curr HIV Res. 7(3): 266-272; Trautmann, et al. (2007) Curr Opin HIV AIDS, 2(3): 219-227; and Petrovas, et al. (2006) J Exp Med. 203(10): 2281-2292, which are herein incorporated by reference. The expression of this TCR-siRNA vector down-regulated PD-1 expression in transduced cells. Therefore, siRNA and/or shRNA may be used to further modify the activity of the cloned TCRs according to the present invention. For example, siRNA and/or shRNA molecules against the programmed death-1 (PD-1) molecule, the T-cell immunoglobulin domain and/or mucin domain 3 (Tim-3) molecule may be included in the vectors described herein.

Recombinant Human Progenitor Cells

Figure 6:
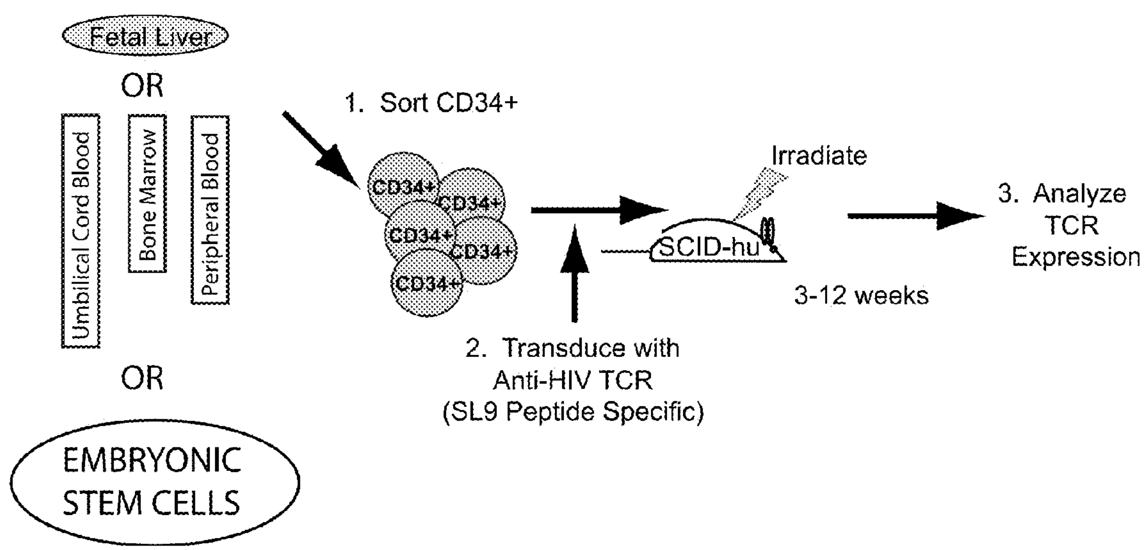
FIG. 6 schematically shows the use of the SCID-hu mouse system to assess human TCR development and functionality.

Human hematopoietic stem cells were then transduced with the codon optimized vector containing the TCRα-2A-TCRβ construct to give recombinant human progenitor cells according to the present invention using methods known in the art. See e.g. Arnold, et al. (2004) J Immunol. 173(5): 3103-3111, which is herein incorporated by reference. In particular, as exemplified herein, human CD34+ hematopoietic stem cells were taken from hematopoietic tissue (e.g. fetal liver) and transduced with the codon optimized vector containing the TCRα-2A-TCRβ construct to give recombinant human progenitor cells. See FIG. 6.

In order to determine whether the recombinant human progenitor cells exhibit CTL activity, the recombinant human progenitor cells and irradiated peripheral blood mononuclear cells (PBMCs) were resuspended in media that contains irradiated HLA-A*0201 cells and 1 μg/ml of antigenic peptide (e.g. the SL9 peptide from HIV) and incubated overnight at 37° C. to prestimulate the cells. After overnight incubation, media containing 50 units/ml of recombinant interleukin (IL)-2 was added. Cells were fed with fresh media every 3 to 4 days, and passaged once every 10 to 14 days. The resulting recombinant human progenitor cells were tested for CTL activity 7 days following passaging by assessing their ability to lyse $^{51}$Chromium-labeled target cells in a standard chromium release assay known in the art. As exemplified herein, the target cells were either HIV infected cells that were matched with HLA-A*0201 or were HLA-A*0201 cells that were pretreated with the SL9 peptide. A recombinant human progenitor cell was designated as having CTL activity if it lysed a target cell.

Engineered Human Thymocytes

The recombinant human progenitor cells were allowed or induced to differentiate and mature into engineered human thymocytes and human T cells that express the transgenic anti-viral TCR. Specifically, the recombinant human progenitor cells were injected directly into the human thymic tissue in sub-lethally irradiated SCID-hu mice. See Amado, et al. (1999) Front Biosci. 4: D468-D475; Kitchen, et al. (2000) J Virol. 74(6): 2943-2948; McCune, J. M. (1992) Bone Marrow Transplant. 9 Suppl 1: 74-76; McCune, et al. (1998) Science. 241(4873): 1632-1639; and Withers-Ward, et al. (1997) Nat Med. 3(10): 1102-1109, which are herein incorporated by reference.

Figure 7:
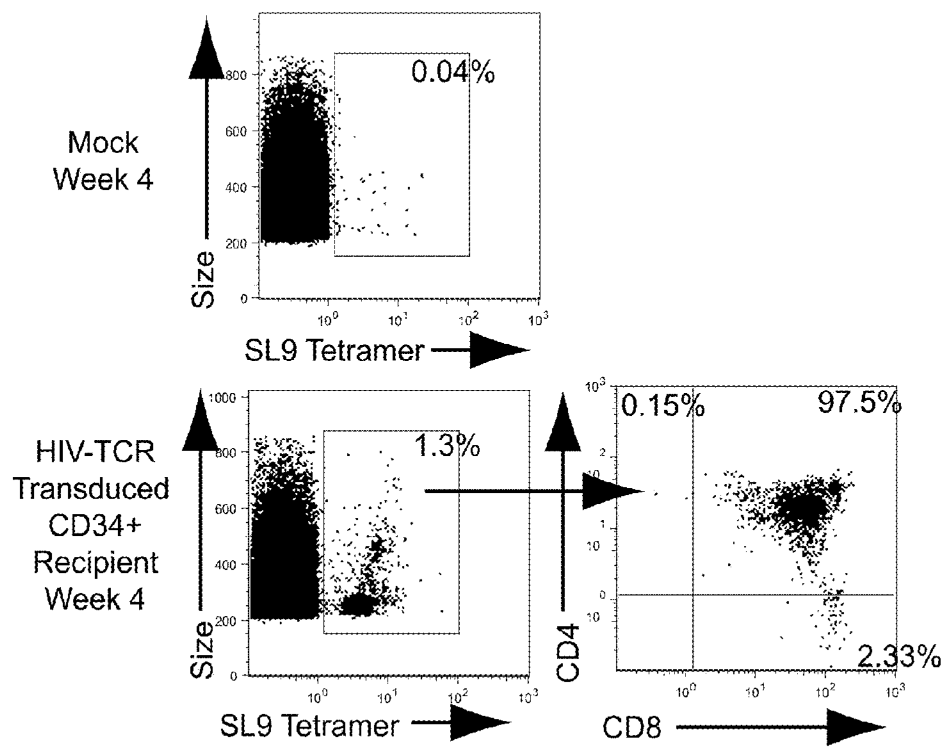
FIG. 7 provides results which demonstrate that human hematopoietic progenitor cells transduced with a human TCR can become immature and mature human thymocytes 4 weeks following transduction and transplantation into human tissue in the SCID-hu mouse, mimicking that of human tissue in the body. At four weeks following implantation with TCR transduced stem cells, human thymic tissue was biopsied and cells were analyzed by flow cytometry for cell size (forward scatter—denoted “Size”) and SL9 specific tetramer staining Mock treated mice (top panels) and mice receiving TCR transduced cells (bottom panels) are indicated. The numbers on the left panels illustrate total SL9 tetramer, or HIV-specific TCR, staining or expressing cells. SL9-tetramer+ cells were gated and the frequency of cells expressing CD4 and/or CD8 are provided in the right panels.
Figure 8:
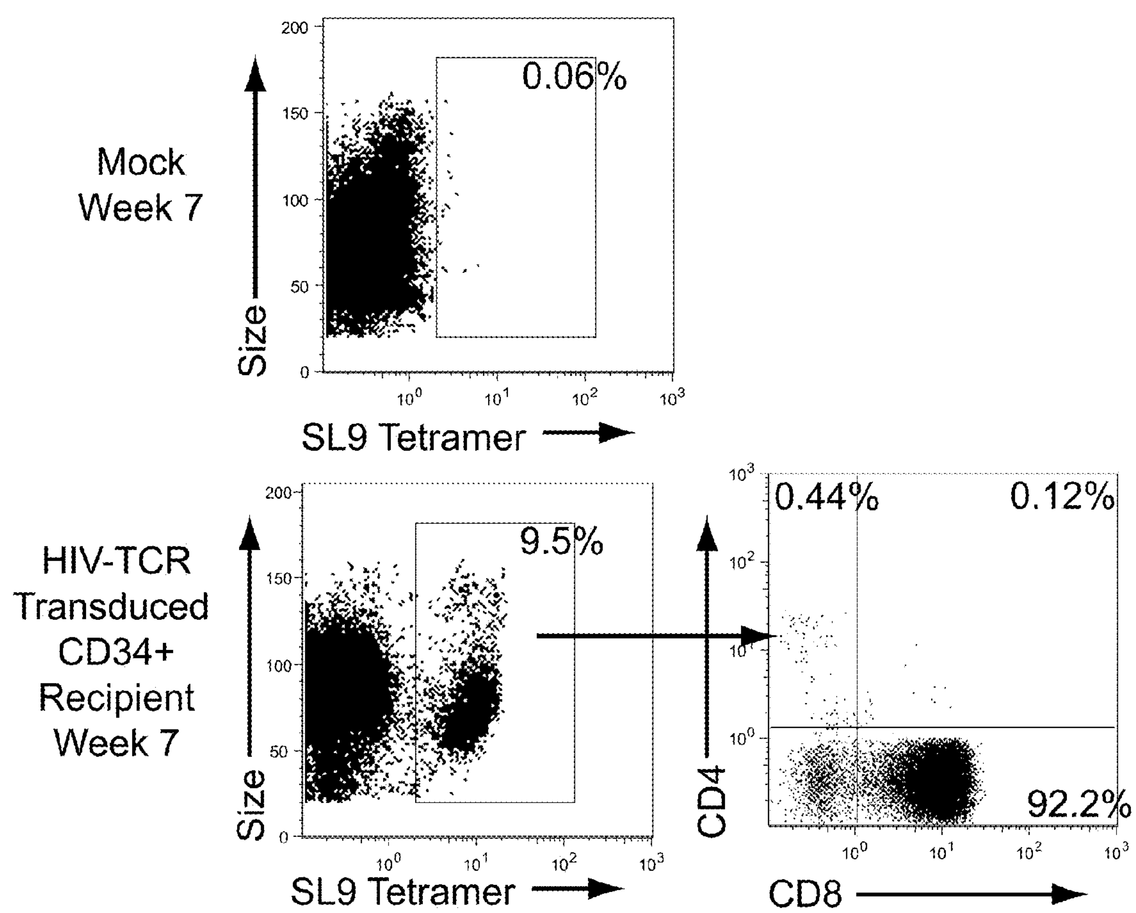
FIG. 8 provides results which demonstrate that human hematopoietic progenitor cells transduced with a human TCR can develop into mature human thymocytes, predominantly CD8+ T cells, 7 weeks following transduction and transplantation into human tissue in the SCID-hu mouse, mimicking that of human tissue in the body. At seven weeks following implantation with TCR transduced stem cells, human thymic tissue was biopsied and cells were analyzed by flow cytometry for cell size (forward scatter—denoted “Size”) and SL9 specific tetramer staining Mock treated mice (top panels) and mice receiving TCR transduced cells (bottom panels) are indicated. The numbers on the left panels illustrate total SL9 tetramer, or HIV-specific TCR, staining or expressing cells. SL9-tetramer+ cells were gated and the frequency of cells expressing CD4 and/or CD8 are provided in the right panels.

The irradiation was performed to clear niches for the newly implanted recombinant human progenitor cells through riddance of endogenous thymocytes. The implanted recombinant human progenitor cells were allowed to develop into engineered human thymocytes for a period of weeks following implantation. Subsequent analysis for markers of developing and mature engineered human thymocytes containing the transgenic SL9-specific TCR was performed following biopsy of the thymic tissue. Within 4 weeks following transplantation of the recombinant human progenitor cells, immature and mature engineered human thymocytes expressing the transgenic SL9-specific TCR were observed through flow cytometric analysis for phenotypic marker expression and through staining the cells with SL9-specific MHC Class 1 tetramer molecules. See FIG. 7. Within 7 weeks following implantation of the recombinant human progenitor cells, significant accumulation of CD8+ thymocytes expressing the transgenic SL9-specific TCR and the exclusion of mature CD4+ cells, thereby indicating correct TCR induced lineage commitment, was observed. See FIG. 8.

Functional Human Thymocytes

Figure 9:
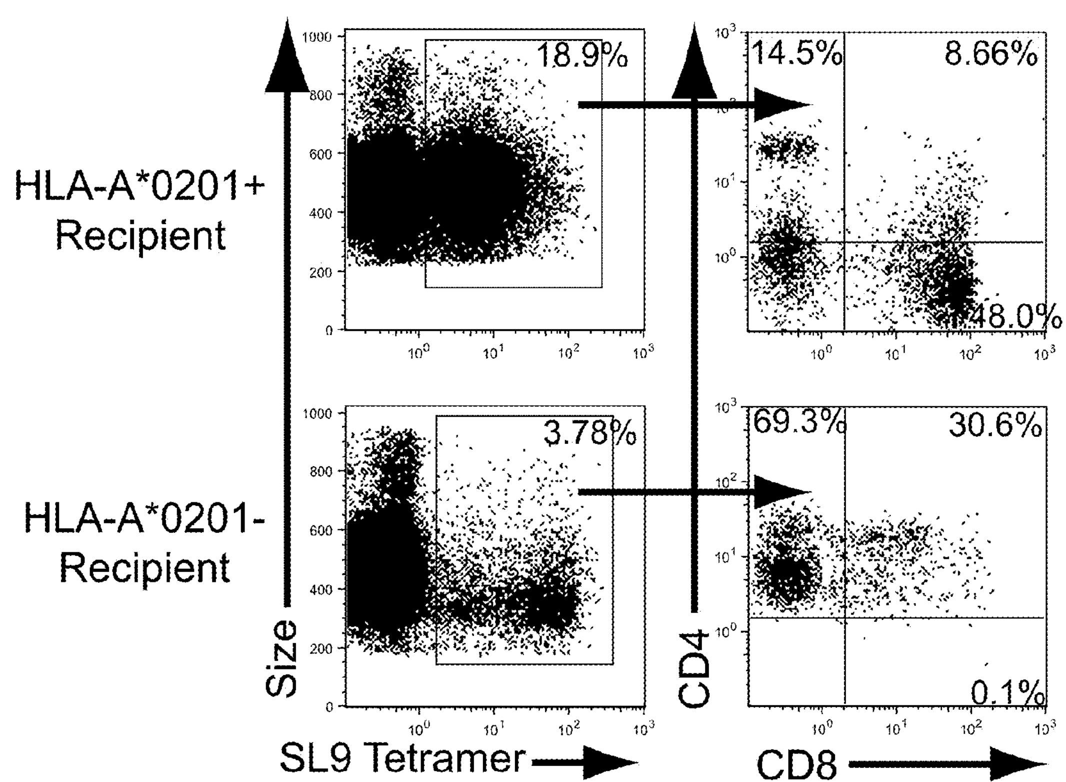
FIG. 9 provides results which demonstrate that a specific human leukocyte antigen (HLA) is required for transgenic TCR containing T cell development into mature CD8+ single positive thymocytes. For the HIV-1 SL9 peptide-specific TCR, HLA-A*201 is a suitable HLA. Fetal liver derived CD34+ HSCs transduced with the SL9-TCR containing lentiviral vector were implanted into mice containing either HLA-A*0201+ thymic tissue (top panels) or into mice containing HLA-A*0201-thymic tissue (bottom panels) and the frequency of SL-9 tetramer+ cells assessed 6 weeks following implantation. Size (forward scatter) versus tetramer staining is presented in the left panels and the values inside the parentheses correspond to the percentage of tetramer positive cells. Tetramer expressing cells in the indicated gate were assessed for CD4 and CD8 expression (right panels) and the frequencies of cells expressing each marker are provided.

To demonstrate the ability of the recombinant human progenitor cells to develop in the presence or absence of the specific SL9 peptide-restricted HLA molecule (HLA-A*0201), the SL9-specific TCR retrovirally transduced CD34+ cells were injected into mice that contained human thymic tissue that was HLA-A*0201+ and mice that contained human thymic tissue that was HLA-A*0201-. HLA-A*0201+ mice developed mature CD8+ T cells that expressed the transgenic SL9-specific TCR, whereas HLA-A*0201− mice did not. See FIG. 9. This evidences that the correct HLA recipient tissue is required for the proper development of the recombinant human progenitor cells into mature human thymocytes and T cells, a process known as positive selection. This data clearly indicates that the HLA-A*0201 molecule is required for stem cells transduced with the SL9-specific TCR to develop properly in the thymus. Thus, engineered human thymocytes resulting from these recombinant human progenitor cells undergo appropriate positive and negative selection. Consequently, mature functional T cells would only be produced in a subject that expresses HLA-A*0201, and would only exercise an antigen-specific immune response if the subject was infected with HIV-1.

Figure 10:
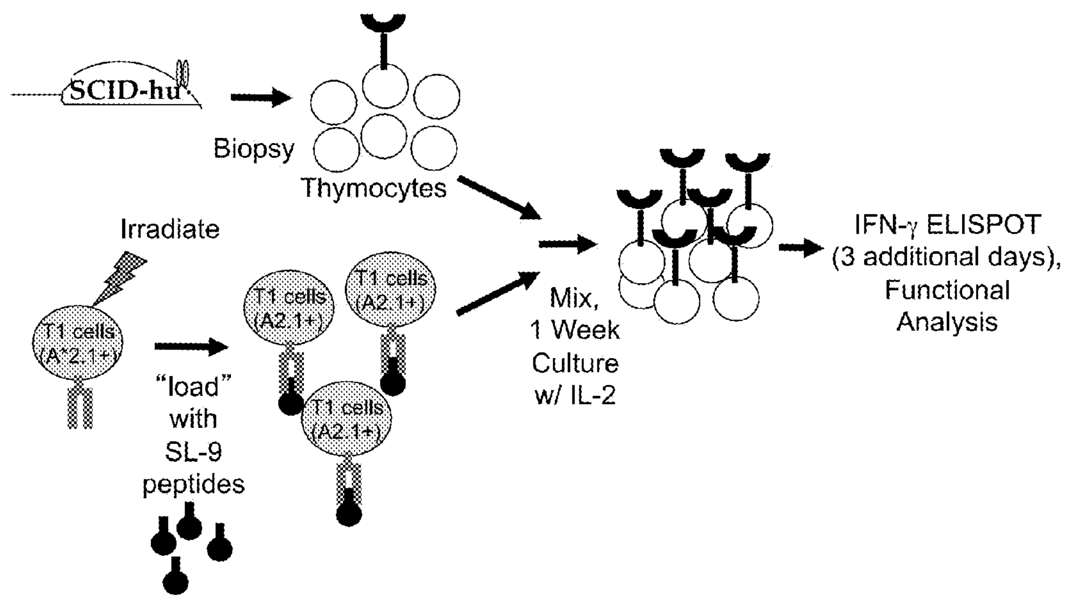
FIG. 10 provides a schematic representation of the strategy used to analyze the functionality of naïve, viral antigen specific T cells displaying the transgenic human TCR.

To demonstrate that the engineered human thymocytes are functional in responding to viral antigen, an assay which pre-stimulates naïve antigen specific thymocytes and assesses functional responses subsequent to cellular activation was conducted. The assay is schematically shown in FIG. 10.

Specifically, thymic tissue from the subject that previously received the recombinant human progenitor cells was biopsied. The naïve engineered human thymocytes obtained therefrom were placed in tissue culture with irradiated antigen presenting cells of a known HLA type, the specific peptide that the transgenic TCR recognizes, and interleukin 2 (IL-2). In particular, naïve engineered human thymocytes from the biopsied thymic tissue were cultured with the HLA-A*0201+ T1 cell line, the SL9 peptide, and IL-2. Following a sufficient period of time in culture which allows the naïve engineered human thymocytes to recognize the specific peptide in the context of the proper HLA molecule and become functionally activated, e.g. 1 week, the engineered human thymocytes were then subjected to further stimulation with the SL9 peptide and assayed for functional cellular responses using methods known in the art.

Figure 11:
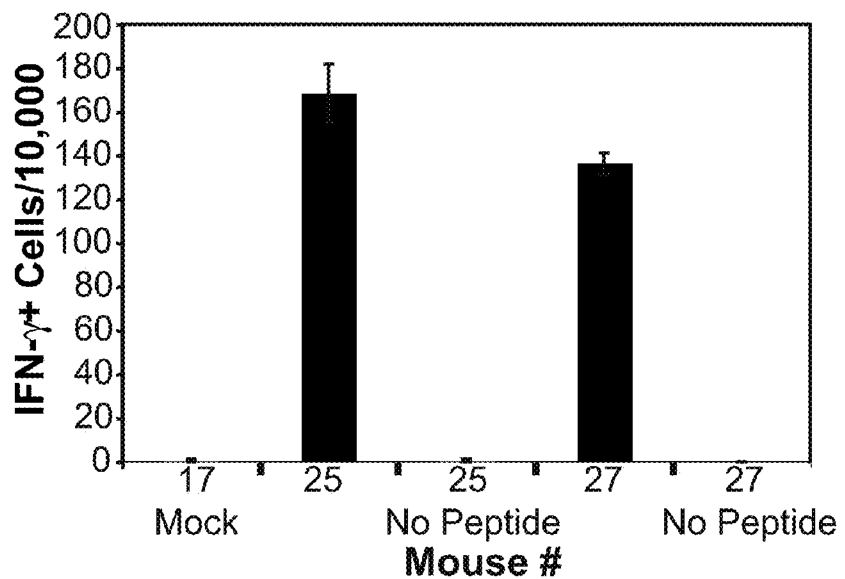
FIG. 11 provides the results which demonstrate the use of ELISPOT in the analysis of transgenic, virus-specific human TCRs that are derived from retroviral transduced human stem cells. Thymic tissues from 2 mice receiving SL9-specific TCR transduced stem cells (mouse #s 25 and 27) and 1 mock-treated mouse (mouse #17) were biopsied 7 weeks following introduction of stem cells and placed into culture with SL9 peptide coated antigen presenting cells for 1 week to allow differentiation from antigen naïve to effector cells. Effector cells were then stimulated with SL9 peptide or medium alone (no peptide) and IFN-γ production was measured by ELISPOT.
Figure 12:
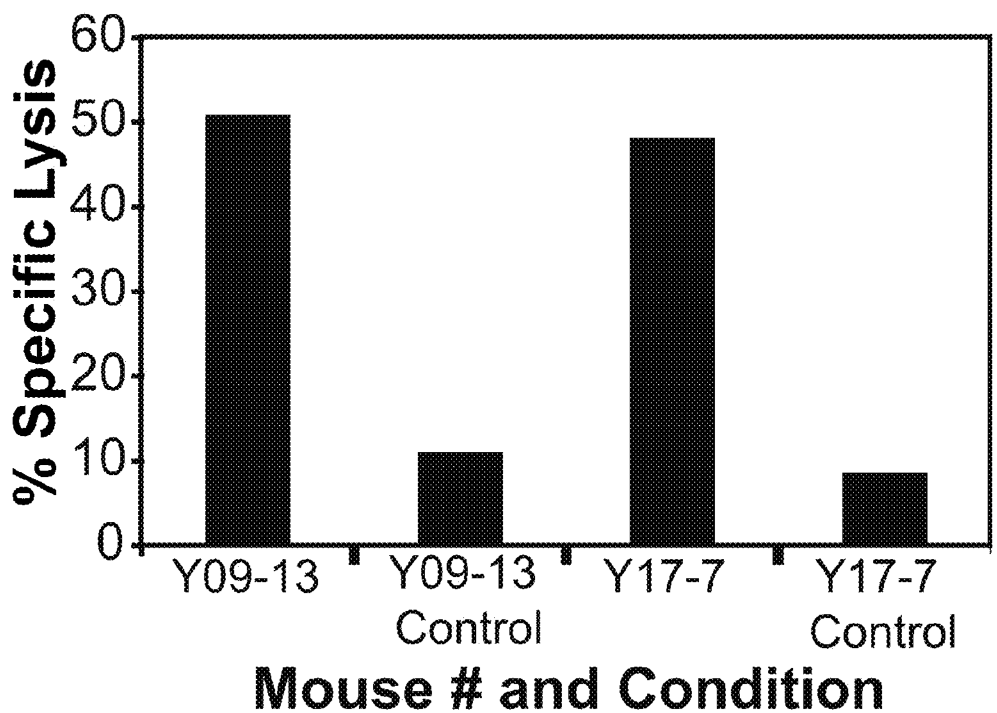
FIG. 12 provides results which demonstrate that newly originated, antigen specific T cells derived from transduced human stem cells can functionally respond to the TCR-specific peptide by producing the cytokine Interferon-gamma. Cells from SCID-hu mice receiving SL9-specific TCR transduced stem cells were obtained by biopsy following differentiation into thymocytes and activated in culture in the presence of an irradiated SL9-peptide coated HLA-A*0201+ B cell line and allogeneic feeder cells. Cells from mouse numbers Y09-13 and Y17-7 were then placed in a standard $^{51}$chromium release assay utilizing SL9 peptide coated T2 cells or untreated T2 cells as a control. Graph shows the specific lytic activity of cells at an effector to target cell ratio of 10:1.

In particular, the engineered human thymocytes were assessed for cytokine production by ELISPOT for interferon gamma (IFN-γ). The results shown in FIG. 11 demonstrate that the recombinant human progenitor cells of the present invention result in engineered human thymocytes that express functional transgenic TCRs. In FIG. 11, the spots on the membranes, which were identified and quantitated, represent engineered human thymocytes that functionally responded specifically to stimulation with the SL9 peptide and produced IFN-γ. FIG. 12 graphically provides the amount of cells per 10,000 total thymocytes that reacted to the SL9 peptide in the ELISPOT assay.

Figure 13:
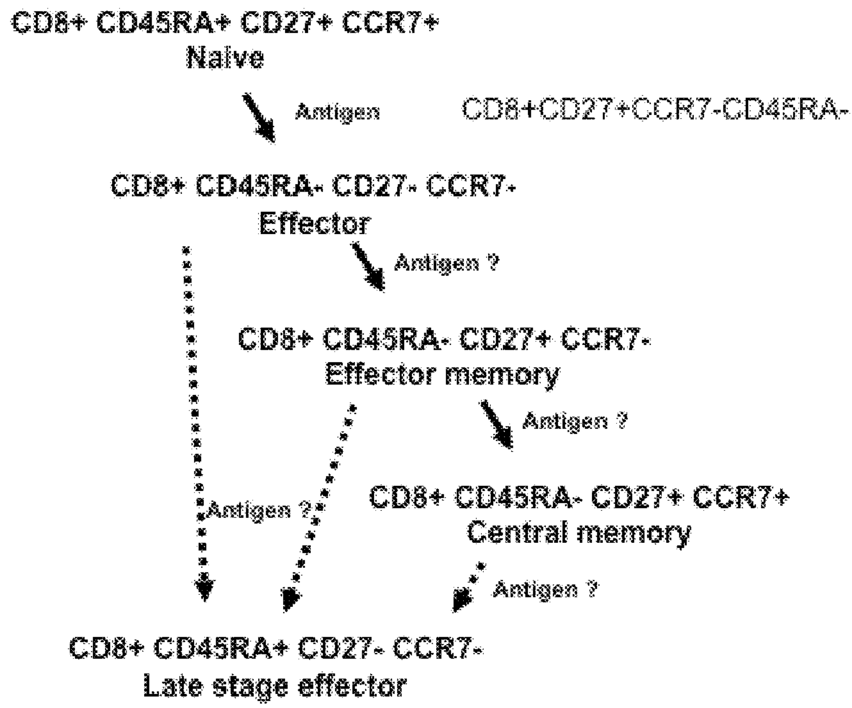
FIG. 13 schematically shows the phenotypic developmental changes that newly stimulated, viral antigen specific TCRs undergo to become functional effector cells in an antigen specific manner.

To further demonstrate that the functionally responding engineered human thymocytes phenotypically represent effector cells, the engineered human thymocytes were stained with antibodies specific for molecules that are indicative of different stages of CD8+ T cell differentiation following antigen stimulation and analyzed by flow cytometry using methods known in the art. See FIG. 13. It was found that these previously naïve engineered human thymocytes acquired a phenotype that represents effector memory type cells 1 week following stimulation with irradiated T1 cells, SL9 peptide, and IL-2.

Functional Human T Cells

Figure 14:
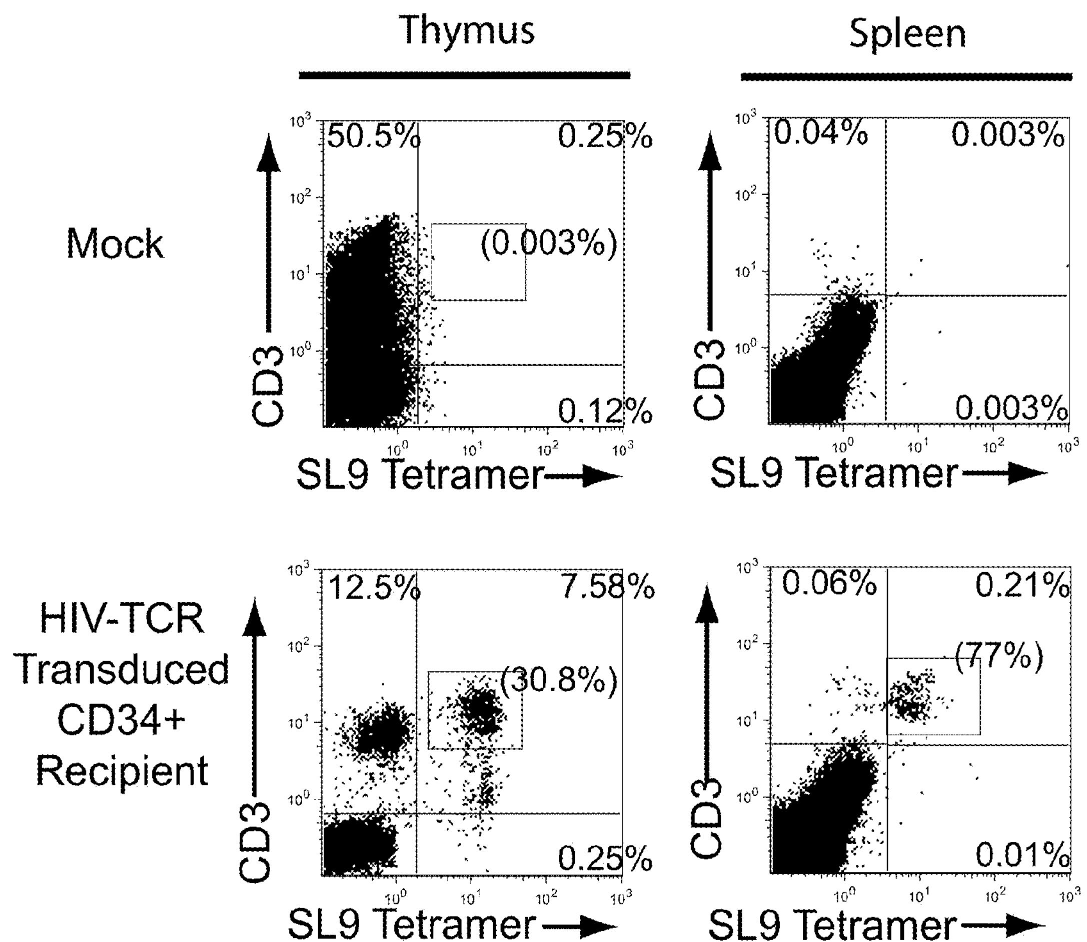
FIG. 14 provides results which demonstrate that human TCR containing T cells are exported from the thymus into the peripheral lymphoid compartments. Mock treated mice (upper row) and mice receiving stem cells transduced with the HIV SL9-specific TCR (lower row) were analyzed 7 weeks following transplantation for CD3 and SL9-specific TCR expression by tetramer staining of cells from the thymus (left panels) or spleen (right panels). The frequency of CD3+ and SL9-tetramer+ cells is provided and the values inside the parentheses correspond to the percentage of tetramer positive cells in the human T cell (CD3+) populations. The presence of cells within these areas indicates that mature cells that express the transgenic TCR can undergo normal developmental mechanisms and are found in the peripheral organs.
Figure 15:
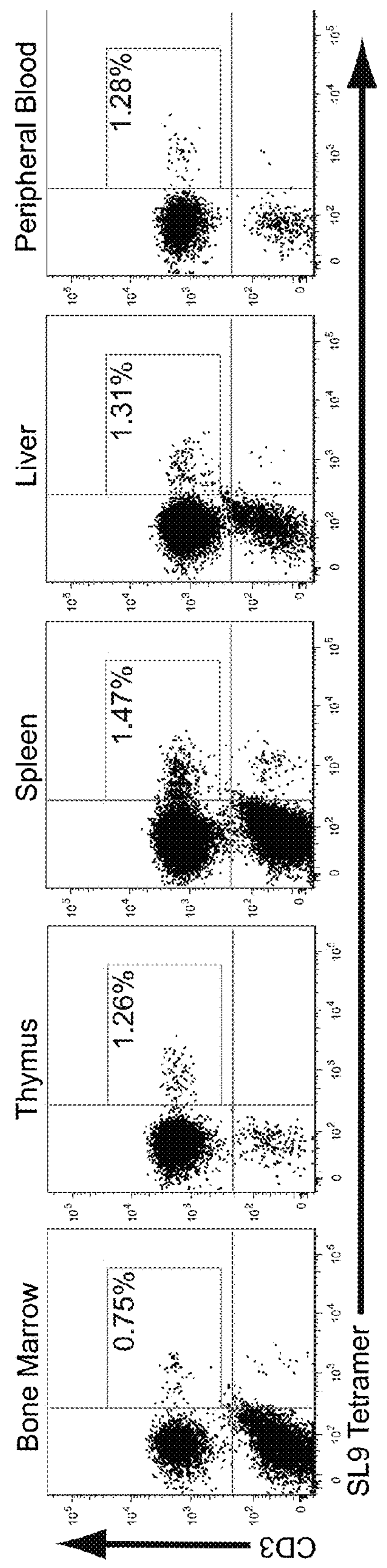
FIG. 15 provides the results which demonstrate that cells expressing the SL-9 TCR are found in multiple organs of a different strain of immunodeficient mice implanted with genetically-modified stem cells. Non-obese diabetic, severe combined immunodeficient, common gamma chain knockout (NSG) mice were implanted with SL9 TCR genetically modified stem cells along with human fetal thymus and liver, known as the Bone marrow, thymus, liver (BLT) humanized mouse. These cells were allowed to engraft and develop in the mouse. Six weeks following implantation, the bone marrow, thymus, spleen, liver, and peripheral blood of the mice were assessed for human cells. This demonstrates the presence of human CD8+ T cells expressing the transgenic TCR in the peripheral organs of the mouse following development from genetically modified stem cells.

Engineered human T cells expressing the transgenic SL9-specific TCR were found in the peripheral organs (e.g. the mouse spleen) of the sub-lethally irradiated SCID-hu mice having the recombinant human progenitor cells directly implanted into the human thymic tissue. See FIG. 14. It was also found that functional engineered human T cells can develop and be exported to the periphery of another type of immunodeficient mouse model, the Non-obese diabetic, Severe combined immunodeficient, common Gamma chain knockout, humanized Bone marrow, fetal Liver, and fetal Thymus (NSG-BLT) mouse that allows the examination of immune responses within the mouse. See FIG. 15. In these studies, recombinant human progenitor cells (i.e. SL9-specific TCR retrovirally transduced human CD34+ cells) were injected intravenously into irradiated immunodeficient mice previously implanted with human fetal thymus and liver. See Melkus, et al. (2006) Nat Med. 12(11): 1316-1322; and Brainard, et al. (2009) J. Virol. 83(14): 7305-7321, which are herein incorporated by reference. In the current experiment, human HLA-A*0201+ fetal liver, containing CD34+ cells modified with the SL9-specific TCR, and thymus tissue were implanted into a NSG strain mouse. Three weeks following this, the mouse was irradiated and intravenously injected with additional, CD34+ cells from the same donor also modified with the SL9-specific TCR. The CD34+ progenitor cells become engrafted in the mouse bone marrow and human liver/thymus tissue and allow human progenitor cells to develop. 6 weeks following injection, engineered human T cells, i.e. SL-9 specific TCR expressing CD8+ T cells, were found in the peripheral blood and other organs following necropsy of the mice by flow cytometry analysis for cell markers and TCR expression. This demonstrates that, when intravenously administered, the recombinant human progenitor cells according to the present invention engraft and result in engineered human T cells that are efficiently exported to the periphery of subjects. Therefore, in the methods of the present invention, the recombinant human progenitor cells may be directly implanted in the thymic tissue of a subject or intravenously administered to the subject in order to result in engraftment and the development of engineered human T cells in the subject.

Figure 16:
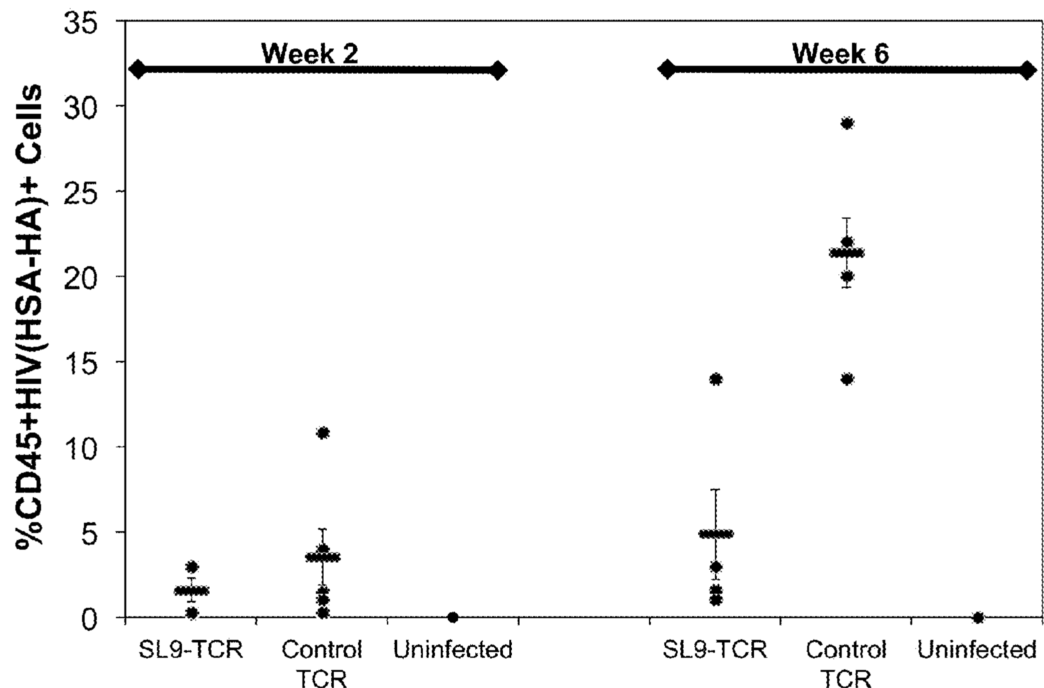
FIG. 16 provides the results which demonstrate the reduction in amount of HIV in mice containing human cells expressing a HIV-specific TCR as compared to uninfected mice or mice containing cells expressing a nonspecific control human TCR two weeks and six weeks following infection. Virally expressing cells were identified by the expression of the marker gene Heat Stable Antigen-Hemagglutinin (HSA-HA) that had previously been cloned into infectious HIV. Humanized BLT mice containing SL9-TCR specific cells or, separately, cells expressing a control non-specific TCR were infected with $HIV_{NL-HSA-HA}$, or left uninfected, following human cell reconstitution. Virally expressing cells were analyzed in the peripheral blood of these mice 2 and 6 weeks following infection by flow cytometry. The figure represents the % of cells expressing HIV at the indicated time in each population of mice. The results demonstrate that mice that express the HIV-specific TCR have lower levels of virally infected cells in the periphery, indicating killing of virally infected cells by the cells expressing the SL9-specific TCR.
Figure 17:
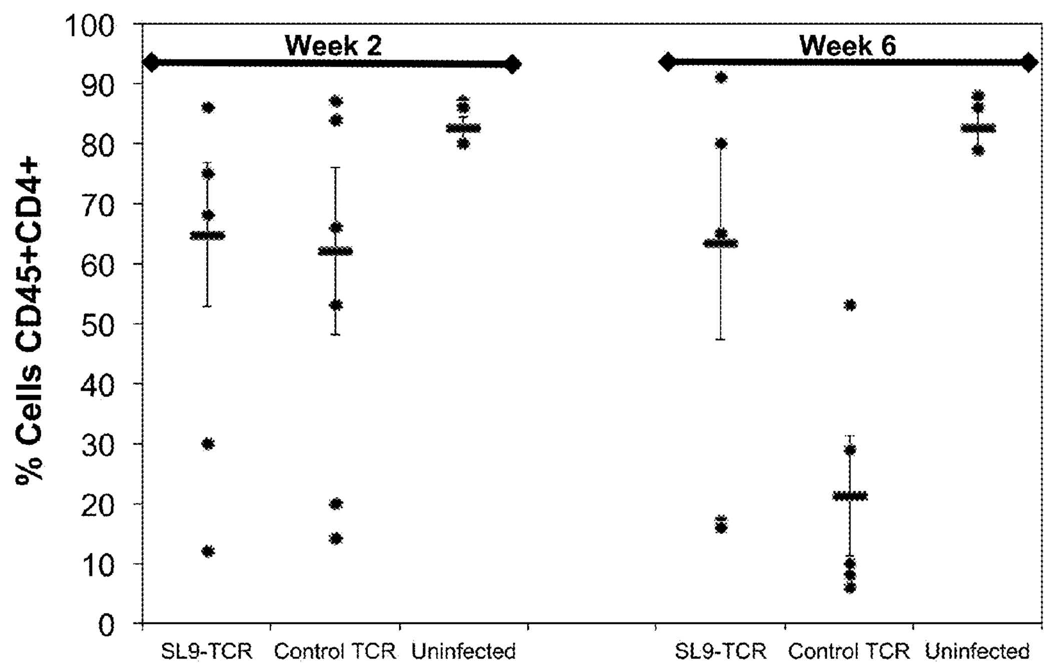
FIG. 17 provides the results which demonstrate the protection of CD4+ T cells in HIV infected mice containing human cells expressing HIV-specific TCR as compared to uninfected mice or HIV infected mice containing cells expressing a nonspecific control human TCR two weeks and six weeks following infection. The same BLT mice infected in FIG. 17 were assessed for CD4 cell percentages two weeks and 6 weeks following infection with HIV by flow cytometry. The results demonstrate that mice the express the HIV-specific TCR have greater percentages of CD4+ T cells in the periphery, indicating protection of these cells from infection with HIV.

The engineered human T cells expressing the SL9-specific TCR were found to be functional in vivo as they were capable of reducing the amount of virally infected cells (FIG. 16) and preventing CD4 T cell loss (FIG. 17) in treated mice following infection with HIV. In these studies, NSG-BLT mice containing human cells genetically modified with the HIV TCR or mice containing cells genetically modified with a non-specific control TCR (as a negative control) were infected with HIV (in this case the HIV-$1_{NL4\text{-}3\text{-}HSA\text{-}HA}$ viral variant. Two weeks and 6 weeks following infection, human cells in the peripheral blood of these mice were analyzed for CD4, CD8 and HSA-HA (viral) expression by flow cytometry. Suppression of virally infected cells (FIG. 16) and protection of CD4+ T cell levels (FIG. 17) was found following infection. These results demonstrate that engineered human T cells according to the present invention that express an HIV-specific TCR can reduce or inhibit HIV replication and reduce or inhibit the loss of target CD4+ T cells in vivo. Therefore, the present invention provides methods for inhibiting, reducing or treating viral infections in a subject which comprise administering recombinant human progenitor cells, engineered human thymocytes, and/or engineered human T cells as described herein. In some embodiments, the amount administered is a therapeutically effective amount, which is an amount that inhibits or reduces viral replication and/or loss of target CD4+ T cells in the subject.

Since a given TCR for an antigen of interest resulting from a given recombinant progenitor cell cannot recognize the antigen of interest when presented by a different HLA molecule, a plurality of recombinant human progenitor cells having different TCRs specific for other peptides presented by different HLA molecules may be made and used in combination in the methods described herein.

In some embodiments, an antigen-specific TCR could be cloned from a subject to be treated, and then it could be introduced into the subject's hematopoietic stem cells. Alternatively, a bank of vectors could be generated following the cloning of many TCRs from a variety of individuals, each of which would be specific for a particular antigen presented in the context of one of the many HLA molecules in the population. These banked TCR gene vectors are preferably stable, and following tissue typing of an individual patient, may be cross-matched for the ability to react with the subject's HLA molecules, and subsequently introduced into the subject's stem cells.

The experiments provided herein evidence that human viral antigen-specific TCRs can be cloned out of immune cells from an infected individual. These TCR clones can then be placed into a gene therapy vector. Human stem cells can then be transduced with the vector and allowed to express the TCR following differentiation and development into mature cells in the presence of the appropriate HLA molecule. The experiments also evidence that the engineered human thymocytes and engineered human T cells expressing a cloned TCR are functional in vivo and are capable of mounting a cellular response against viruses having the antigen to which the cloned TCR is specific against. Therefore, the present invention provides methods for treating a viral infection, such as an HIV infection, in a subject.

For example, in some embodiments, peripheral blood is removed from a human subject having the viral infection and one or more viral antigen specific cells are identified. A T cell receptor (TCR) from one of the viral antigen specific cells is cloned through spectratyping-based cloning. The α- and β-subunits of the virus specific TCR is cloned into a vector that allows its concurrent expression in human cells. A viral gene therapy vector, which may be the same or different from the cloning vector, containing the cloned virus-specific TCR is obtained. In some embodiments, the vector is one that expresses a virus-specific TCR restricted to one of the class I HLA molecules of the human subject to be treated.

Human autologous or histocompatible stem cells are then transduced with the vector containing the cloned virus antigen specific TCR to give a recombinant human progenitor cell. The transduction efficiency may validated and the recombinant human progenitor cells can be analyzed. The recombinant human progenitor cells are transplanted into the human subject to be treated where the recombinant human progenitor cells differentiate and mature into engineered human thymocytes and engineered human T cells that express the cloned TCR. Engraftment of the transplanted recombinant human progenitor cells may be determined. The functional responses of the recombinant human progenitor cells, the engineered human thymocytes and/or the engineered human T cells may be monitored. Virus-specific immune responses and the clearance of the virus from the body may be monitored. Virus epitope mutation, especially the transgenic TCR-specific epitope, may be determined. In some embodiments, if "virologic failure" or "immune failure" is detected, the process may be repeated with the same or different viral antigen-specific TCR. In embodiments, where no virologic or immune failure is detected, the subject may undergo further monitoring until, for example, the infection is controlled or cleared.

In some embodiments, the gene therapy vector containing the TCR clone may be administered to the subject. Alternatively, engineered human thymocytes and/or engineered human T cells expressing the TCR clone may be administered to the subject. In some embodiments, a plurality of different recombinant human progenitor cells, a plurality of different engineered human thymocytes and/or a plurality of different engineered human T cells may be employed.

Additional Embodiments

Figure 18:
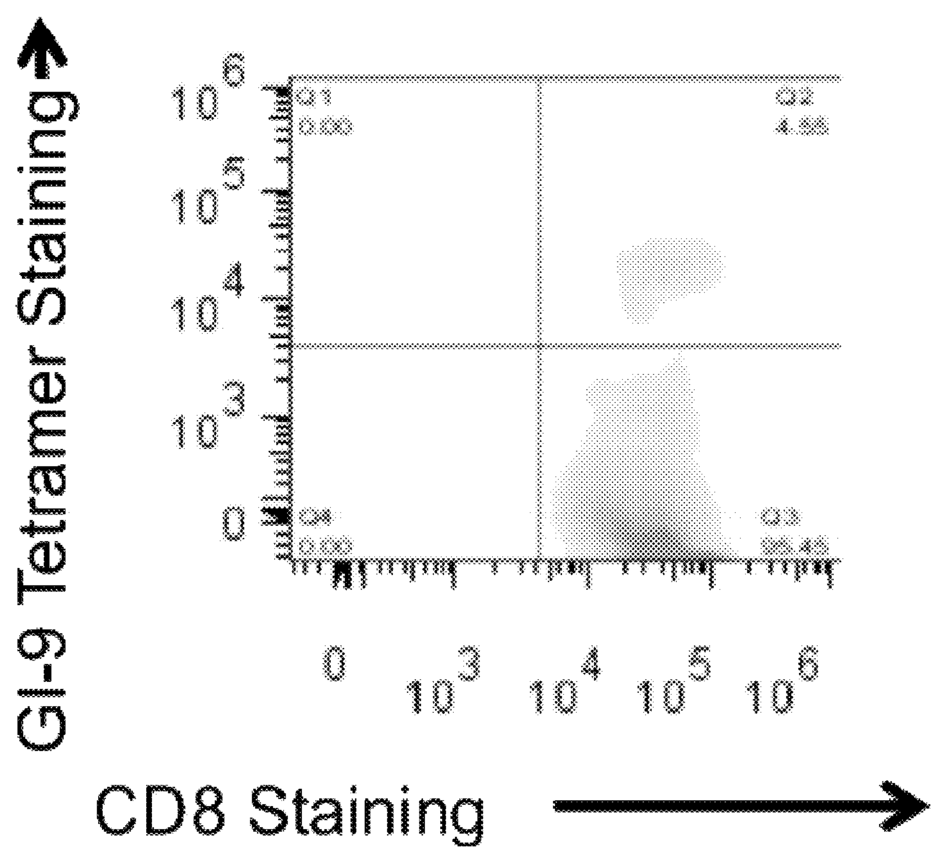
FIG. 18 provides the results which demonstrate the molecular cloning and expression of a human TCR specific to a different viral antigen. Peripheral blood mononuclear cells from an HLA-A*0201, previously influenza infected individual were removed and stimulated with influenza peptide antigen (the GILGFVFTL matrix peptide (SEQ ID NO:39)). The TCR responding to this peptide was molecularly cloned by the spectratyping process and expressed by genetically modified CD8+ T cells from another individual. The figure represents MHC tetramer staining of the expressed TCR, indicating successful cloning and expression of a TCR specific to influenza.

In addition to the recombinant progenitor cells, engineered thymocytes, and engineered T cells which express TCRs specific to the SL9 peptide as exemplified herein, recombinant human progenitor cells, engineered human thymocytes, and engineered human T cells which express other TCRs, i.e. TCRs which are specific for other antigens, are contemplated herein. For example, a TCR specific for an influenza antigen (in this case the influenza A matrix protein 58-68 or GI-9) was cloned and recombinant human progenitor cells, engineered human thymocytes, and engineered human T cells which express the cloned TCR were created using the methods described herein. See FIG. 18. Briefly, PBMCs were taken from an HLA-A*0201+ subject who was previously exposed to influenza. Cells were then cultured in the presence and absence of the GI-9 peptide, to allow selection for the cells expressing the antigen specific TCR. Spectratyping-based cloning was then used to rapidly identify, sequence, and clone a TCR specific to the influenza GI-9 peptide.

Therefore, some embodiments, the target antigen comprises, consists essentially of, or consists of an epitope selected from the group consisting of SL9 (SLYNTVATL (SEQ ID NO:1)), GE11 (GHQAAMQMLKE (SEQ ID NO:2)), AL9-Vpr (AIIRILQQL (SEQ ID NO:3)), RI9-Vpr (RILQQLLFI (SEQ ID NO:4)), AL9-Nef (AFHHMAREL (SEQ ID NO:5)), and QL10-GP160 (QELKNSAVSL (SEQ ID NO:6)).

In some embodiments, the present invention provides a polypeptide, which may be isolated or purified, comprising, consisting essentially of, or consisting of a first sequence having a 90%, 91%, 92%, 93%, 94%, 95%, 96%, 97%, 98%, 99%, or 100% identity to MMKSLRVLLVILWLQLSWVWSQQKEVEQNSGPLSVPEGAIASLNCTYSDR
GSQSFFWYRQYSGKSPELIMSIYSNGDKEDGRFTAQLNKASQYVSLLIRD
SQPSDSATYLCAVISNSGNTPLVFGKGTRLSVIANIQNPDPAVYQLRDSK
SSDKSVCLFTDFDSQTNVSQSKDSDVYITDKTVLDMRSMDFKSNSAVAWS
NKSDFACANAFNNSIIPEDTFFPSPESSCDVKLVEKSFETDTNLNFQNLS
VIGFRILLLKVAGFNLLMTLRLWSS (a TCR α subunit for HIV, SEQ ID NO:7, variable region underlined) and a second sequence having a 90%, 91%, 92%, 93%, 94%, 95%, 96%, 97%, 98%, 99%, or 100% identity to MGSRLLCWVLLCLLGAGPVKAGVTQTPRYLIKTRGQQVTLSCSPISGHRS
VSWYQQTPGQGLQFLFEYFSETQRNKGNFPGRFSGRQFSNSRSEMNVSTL
ELGDSALYLCASSFDSEQYFGPGTRLTVTEDLKNVFPPEVAVFEPSEAEI
SHTQKATLVCLATGFYPDHVELSWWVNGKEVHSGVCTDPQPLKEQPALND
SRYCLSSRLRVSATFWQNPRNHFRCQVQFYGLSENDEWTQDRAKPVTQIV
SAEAWGRADCGFTSESYQQGVLSATILYEILLGKATLYAVLVSALVLMAM
VKRKDSRG (a TCR β subunit for HIV, SEQ ID NO:8, variable region underlined).

In some embodiments, the present invention provides an isolated or purified polypeptide comprising, consisting essentially of, or consisting of a first sequence having a 90%, 91%, 92%, 93%, 94%, 95%, 96%, 97%, 98%, 99%, or 100% identity to MQLLEQSPQFLSIQEGENLTVYCNSSSVFSSLQWYRQEPGEGPVLLVTVV
TGGEVKKLKRLTFQFGDARKDSSLHITAAQPGDTGLYLCAGAGSQGNLIF
GKGTKLSVKPNIQNPDPAVYQLRDSKSSDKSVCLFTDFDSQTNVSQSKDS
DVYITDKTVLDMRSMDFKSNSAVAWSNKSDFACANAFNNSIIPEDTFFPS
PESSCDVKLVEKSFETDTNLNFQNLSVIGFRILLLKVAGFNLLMTLRLWS
S (a TCR α subunit for an influenza epitope, SEQ ID NO:9, variable region underlined); and a second sequence having a 90%, 91%, 92%, 93%, 94%, 95%, 96%, 97%, 98%, 99%, or 100% identity to MVDGGITQSPKYLFRKEGQNVTLSCEQNLNHDAMYWYRQDPGQGLRLIYY
SQIVNDFQKGDIAEGYSVSREKKESFPLTVTSAQKNPTAFYLCASSSRSS
YEQYFGPGTRLTVTEDLKNVFPPEVAVFEPSEAEISHTQKATLVCLATGF
YPDHVELSWWVNGKEVHSGVSTDPQPLKEQPALNDSRYSLSSRLRVSATF
WQNPRNHFRCQVQFYGLSENDEWTQDRAKPVTQIVSAEAWGRADCGFTSE
SYQQGVLSATILYEILLGKATLYAVLVSALVLMAMQEKGFQR (TCR β subunit for an influenza epitope, SEQ ID NO:10, variable region underlined).

Other TCR clones obtained by the methods described herein include a polypeptide comprising, consisting essentially of, or consisting of:

a) a first sequence having a 90%, 91%, 92%, 93%, 94%, 95%, 96%, 97%, 98%, 99%, or 100% identity to MVLKFSVSILWIQLAWVSTQLLEQSPQFLSIQEGENLTVYCNSSSVFSSL
QWYRQEPGEGPVLLVTVVTGGEVKKLKRLTFQFGDARKDSSLHITAAQPG
DTGLYLCAGAGWRDDKIIFGKGTRLHILPNIQNPDPAVYQLRDSKSSDKS
VCLFTDFDSQTNVSQSKDSDVYITDKTVLDMRSMDFKSNSAVAWSNKSDF
ACANAFNNSIIPADTFFPSPESSCDVKLVEKSFETDTNLNFQNLSVIGFR
ILLLKVAGFNLLMTLRLWSS (a TCR α subunit for GE11 in HIV Gag, SEQ ID NO:11, variable region underlined) or MAMLLGASVLILWLQPDWVNSQQKNDDQQVKQNSPSLSVQEGRISILNCD
YTNSMFDYFLWYKKYPAEGPTFLISISSIKDKNEDGRFTVFLNKSAKHLS
LHIVPSQPGDSAVYFCAANSLDRDDKIIFGKGTRLHILPNIQNPDPAVYQ
LRDSKSSDKSVCLFTDFDSQTNVSQSKDSDVYITDKTVLDMRSMDFKSNS
AVAWSNKSDFACANAFNNSIIPADTFFPSPESSCDVKLVEKSFETDTNLN
FQNLSVIGFRILLLKVAGFNLLMTLRLWSS (a TCR α subunit for GE11 in HIV Gag, SEQ ID NO:12, variable region underlined) and a second sequence having a 90%, 91%, 92%, 93%, 94%, 95%, 96%, 97%, 98%, 99%, or 100% identity to MLSLLLLLLGLSVFSAVISQKPSRDICQRGTSLTIQCQVDSQVTMMFWYR
QQPGQSLTLIATANQGSEATYESGFVIDKFPISRPNLTFSTLTVSNMSPE
DSSIYLCSVGPRQGGEQYFGPGTRLTVTEDLNKVFPPEVAVFEPSEAEIS
HTQKATLVCLATGFFPDHVELSWWVNGKEVHSGVSTDPQPLKEQPALNDS
RYCLSSRLRVSATFWQNPRNHFRCQVQFYGLSENDEWTQDRAKPVTQIVS
AEAWGRADCGFTSVSYQQGVLSATILYEILLGKATLYAVLVSALVLMAMV
KRKDF (a TCR β subunit for GE11 in HIV Gag, SEQ ID NO:13, variable region underlined);

b) a first sequence having a 90%, 91%, 92%, 93%, 94%, 95%, 96%, 97%, 98%, 99%, or 100% identity to MKLVTSITVLLSLGIMGDAKTTQPNSMESNEEEPVHLPCNHSTISGTDYI
HWYRQLPSQGPEYVIHGLTSNVNNRMASLAIAEDRKSSTLILHRATLRDA
AVYYCILIPPPYSGAGSYQLTFGKGTKLSVIPNIQNPDPAVYQLRDSKSS
DKSVCLFTDFDSQTNVSQSKDSDVYITDKTVLDMRSMDFKSNSAVAWSNK
SDFACANAFNNSIIPADTFFPSPESSCDVKLVEKSFETDTNLNFQNLSVI
GFRILLLKVAGFNLLMTLRLWSS (a TCR α subunit for the AL9 epitope of HIV Vpr, SEQ ID NO:14, variable region underlined) and a second sequence having a 90%, 91%, 92%, 93%, 94%, 95%, 96%, 97%, 98%, 99%, or 100% identity to MLSPDLPDSAWNTRLLCHVMLCLLGAVSVAAGVIQSPRHLIKEKRETATL
KCYPIPRHDTVYWYQQGPGQDPQFLISFYEKMQSDKGSIPDRFSAQQFSD
YHSELNMSSLELGDSALYFCASSSLRAASYGYTFGSGTRLTVVEDLNKVF
PPEVAVFEPSEAEISHTQKATLVCLATGFFPDHVELSWWVNGKEVHSGVS
TDPQPLKEQPALNDSRYCLSSRLRVSATFWQNPRNHFRCQVQFYGLSEND
EWTQDRAKPVTQIVSAEAWGRADCGFTSVSYQQGVLSATILYEILLGKAT
LYAVLVSALVLMAMVKRKDF (a TCR β subunit for the AL9 epitope of HIV Vpr, SEQ ID NO:15, variable region underlined); or MGTSLLCWMALCLLGADHADTGVSQDPRHKITKRGQNVTFRCDPISEHNR
LYWYRQTLGQGPEFLTYFQNEAQLEKSRLLSDRFSAERPKGSFSTLEIQR
TEQGDSAMYLCASSSQAVSTDTQYFGPGTRLTVLEDLNKVFPPEVAVFEP
SEAEISHTQKATLVCLATGFFPDHVELSWWVNGKEVHSGVSTDPQPLKEQ
PALNDSRYCLSSRLRVSATFWQNPRNHFRCQVQFYGLSENDEWTQDRAKP
VTQIVSAEAWGRADCGFTSVSYQQGVLSATILYEILLGKATLYAVLVSAL
VLMAMVKRKDF (a TCR β subunit for the AL9 epitope of HIV Vpr, SEQ ID NO:16, variable region underlined);

c) a first sequence having a 90%, 91%, 92%, 93%, 94%, 95%, 96%, 97%, 98%, 99%, or 100% identity to MLLLLIPVLGMIFALRDARAQSVSQHNHHVILSEAASLELGCNYSYGGTV
NLFWYVQYPGQHLQLLLKYFSGDPLVKGIKGFEAEFIKSKFSFNLRKPSV
QWSDTAEYFCAVIEDSSYKLIFGSGTRLLVRPDIQNPDPAVYQLRDSKSS
DKSVCLFTDFDSQTNVSQSKDSDVYITDKTVLDMRSMDFKSNSAVAWSNK
SDFACANAFNNSIIPEDTFFPSPESSCDVKLVEKSFETDTNLNFQNLSVI
GFRILLLKVAGFNLLMTLRLWSS (a TCR α subunit for the SL9 epitope of HIV Gag, SEQ ID NO:17, variable region underlined) and a second sequence having a 90%, 91%, 92%, 93%, 94%, 95%, 96%, 97%, 98%, 99%, or 100% identity to MGTRLLCWAALCLLGAELTEAGVAQSPRYKIIEKRQSVAFWCNPISGHAT
LYWYQQILGQGPKLLIQFQNNGVVDDSQLPKDRFSAERLKGVDSTLKIQP
AKLEDSAVYLCASSLEHEQYFGPGTRLTVTEDLKNVFPPEVAVFEPSEAE
ISHTQKATLVCLATGFYPDHVELSWWVNGKEVHSGVSTDPQPLKEQPALN
DSRYCLSSRLRVSATFWQNPRNHFRCQVQFYGLSENDEWTQDRAKPVTQI
VSAEAWGRADCGFTSESYQQGVLSATILYEILLGKATLYAVLVSALVLMA
MQEKGFQR (a TCR β subunit for the SL9 epitope of HIV Gag, SEQ ID NO:18, variable region underlined);

d) a first sequence having a 90%, 91%, 92%, 93%, 94%, 95%, 96%, 97%, 98%, 99%, or 100% identity to MLLLLVPVLEVIFTLGGTRAQSVTQLGSHVSVSEGALVLLRCNYSSSVPP
YLFWYVQYPNQGLQLLLKYTTGATLVKGINGFEAEFKKSETSFHLTKPSA
HMSDAAEYFCAVSEIEFGNEKLTFGTGTRLTIIPNIQNPDPAVYQLRDSK
SSDKSVCLFTDFDSQTNVSQSKDSDVYITDKTVLDMRSMDFKSNSAVAWS
NKSDFACANAFNNSIIPEDTFFPSPESSCDVKLVEKSFETDTNLNFQNLS
VIGFRILLLKVAGFNLLMTLRLWSS (a TCR α subunit for the AL9 epitope of HIV Nef, SEQ ID NO:19, variable region underlined) and a second sequence having a 90%, 91%, 92%, 93%, 94%, 95%, 96%, 97%, 98%, 99%, or 100% identity to MGTRLLCWVVLGFLGTDHTGAGVSQSPRYKVAKRGQDVALRCDPISGHVS
LFWYQQALGQGPEFLTYFQNEAQLDKSGLPSDRFFAERPEGSVSTLKIQR
TQQEDSAVYLCASSAGLGTGTSYEQYFGPGTRLTVTEDLKNVFPPEVAVF
EPSEAEISHTQKATLVCLATGFYPDHVELSWWVNGKEVHSGVCTDPQPLK
EQPALNDSRYCLSSRLRVSATFWQNPRNHFRCQVQFYGLSENDEWTQDRA
KPVTQIVSAEAWGRADCGFTSESYQQGVLSATILYEILLGKATLYAVLVS
ALVLMAMVKRKDSRG (a TCR β subunit for the AL9 epitope of HIV Nef, SEQ ID NO:20, variable region underlined);

e) a first sequence having a 90%, 91%, 92%, 93%, 94%, 95%, 96%, 97%, 98%, 99%, or 100% identity to MAMLLGASVLILWLQPDWVNSQQKNDDQQVKQNSPSLSVQEGRISILNCD
YTNSMFDYFLWYKKYPAEGPTFLISISSIKDKNEDGRFTVFLNKSAKHLS
LHIVPSQPGDSAVYFCAASPFLSTGANSKLTFGKGITLSRPDIQNPDPAV
YQLRDSKSSDKSVCLFTDFDSQTNVSQSKDSDVYITDKTVLDMRSMDFKS
NSAVAWSNKSDFACANAFNNSIIPEDTFFPSPESSCDVKLVEKSFETDTN
LNFQNLSVIGFRILLLKVAGFNLLMTLRLWSS (a TCR α subunit for the RI9 epitope of HIV Vpr, SEQ ID NO:21, variable region underlined) and a second sequence having a 90%, 91%, 92%, 93%, 94%, 95%, 96%, 97%, 98%, 99%, or 100% identity to MGTRLLCWAALCLLGAELTEAGVAQSPRYKIIEKRQSVAFWCNPISGHAT
LYWYQQILGQGPKLLIQFQNNGVVDDSQLPKDRFSAERLKGVDSTLKIQP
AKLEDSAVYLCASSLEHEQYFGPGTRLTVTEDLKNVFPPEVAVFEPSEAE
ISHTQKATLVCLATGFYPDHVELSWWVNGKEVHSGVCTDPQPLKEQPALN
DSRYCLSSRLRVSATFWQNPRNHFRCQVQFYGLSENDEWTQDRAKPVTQI
VSAEAWGRADCGFTSESYQQGVLSATILYEILLGKATLYAVLVSALVLMA
MVKRKDSRG (a TCR β subunit for the RI9 epitope of HIV Vpr, SEQ ID NO:22, variable region underlined);

f) a first sequence having a 90%, 91%, 92%, 93%, 94%, 95%, 96%, 97%, 98%, 99%, or 100% identity to MAGIRALFMYLWLQLDWVSRGESVGLHLPTLSVQEGDNSIINCAYSNSAS
DYFIWYKQESGKGPQFIIDIRSNMDKRQGQRVTVLLNKTVKHLSLQIAAT
QPGDSAVYFCAERAGNQFYFGTGTSLTVIPNIQNPDPAVYQLRDSKSSDK
SVCLFTDFDSQTNVSQSKDSDVYITDKTVLDMRSMDFKSNSAVAWSNKSD
FACANAFNNSIIPEDTFFPSPESSCDVKLVEKSFETDTNLNFQNLSVIGF
RILLLKVAGFNLLMTLRLWSS (a TCR α subunit for the SL9 epitope of HIV p17, SEQ ID NO:23, variable region underlined) and a second sequence having a 90%, 91%, 92%, 93%, 94%, 95%, 96%, 97%, 98%, 99%, or 100% identity to MSNQVLCCVVLCFLGANTVDGGITQSPKYLFRKEGQNVTLSCEQNLNHDA
MYWYRQDPGQGLRLIYYSQIVNDFQKGDIAEGYSVSREKKESFPLTVTSA
QKNPTAFYLCASKAGGMTEAFFGQGTRLTVVEDLKNVFPPEVAVFEPSEA
EISHTQKATLVCLATGFYPDHVELSWWVNGKEVHSGVCTDPQPLKEQPAL
NDSRYCLSSRLRVSATFWQNPRNHFRCQVQFYGLSENDEWTQDRAKPVTQ
IVSAEAWGRADCGFTSESYQQGVLSATILYEILLGKATLYAVLVSALVLM
AMVKRKDSRG (a TCR β subunit for the SL9 epitope of HIV p17, SEQ ID NO:24, variable region underlined);

g) a first sequence having a 90%, 91%, 92%, 93%, 94%, 95%, 96%, 97%, 98%, 99%, or 100% identity to MKSLRVLLVILWLQLSWVWSQQKEVEQNSGPLSVPEGAIASLNCTYSDRG
SQSFFWYRQYSGKSPELIMFIYSNGDKEDGRFTAQLNKASQYVSLLIRDS
QPSDSATYLCAVIGNAGNMLTFGGGTRLMVKPHIQNPDPAVYQLRDSKSS
DKSVCLFTDFDSQTNVSQSKDSDVYITDKTVLDMRSMDFKSNSAVAWSNK
SDFACANAFNNSIIPEDTFFPSPESSCDVKLVEKSFETDTNLNFQNLSVI
GFRILLLKVAGFNLLMTLRLWSS (a TCR α subunit for the QL10 epitope of HIV GP160, SEQ ID NO:25, variable region underlined) or MWGVFLLYVSMKMGGTTGQNIDQPTEMTATEGAIVQINCTYQTSGFNGLF
WYQQHAGEAPTFLSYNVLDGLEEKGRFSSFLSRSKGYSYLLLKELQMKDS
ASYLCAVSDGGLNTDKLIFGTGTRLQVFPNIQNPDPAVYQLRDSKSSDKS
VCLFTDFDSQTNVSQSKDSDVYITDKTVLDMRSMDFKSNSAVAWSNKSDF
ACANAFNNSIIPEDTFFPSPESSCDVKLVEKSFETDTNLNFQNLSVIGFR
ILLLKVAGFNLLMTLRLWSS (a TCR α subunit for the QL10 epitope of HIV GP160, SEQ ID NO:26, variable region underlined) and a second sequence having a 90%, 91%, 92%, 93%, 94%, 95%, 96%, 97%, 98%, 99%, or 100% identity to MGFRLLCCVAFCLLGAGPVDSGVTQTPKHLITATGQRVTLRCSPRSGDLS
VYWYQQSLDQGLQFLIHYYNGEERAKGNILERFSAQQFPDLHSELNLSSL
ELGDSALYFCASSVALETPYILEREVGSQDLKNVFPPEVAVFEPSEAEIS
HTQKATLVCLATGFYPDHVELSWWVNGKEVHSGVCTDPQPLKEQPALNDS
RYCLSSRLRVSATFWQNPRNHFRCQVQFYGLSENDEWTQDRAKPVTQIVS
AEAWGRADCGFTSESYQQGVLSATILYEILLGKATLYAVLVSALVLMAMV
KRKDSRG (a TCR β subunit for the QL10 epitope of HIV GP160, SEQ ID NO:27, variable region underlined);

h) a first sequence having a 90%, 91%, 92%, 93%, 94%, 95%, 96%, 97%, 98%, 99%, or 100% identity to LMKSLRVLLVILWLQLSWVWSQQKEVEQNSGPLSVPEGAIASLNCTYSDR
GSQSFFWYRQYSGKSPELIMSIYSNGDKEDGRFTAQLNKASQYVSLLIRD
SQPSDSATYLCAVISNSGNTPLVFGKGTRLSVIANIQNPDPAVYQLRDSK
SSDKSVCLFTDFDSQTNVSQSKDSDVYITDKCVLDMRSMDFKSNSAVAWS
NKSDFACANAFNNSIIPEDTFFPSPESSCDVKLVEKSFETDTNLNFQNLS
VIGFRILLLKVAGFNLLMTLRLWSS (a TCR α subunit for the SL9 epitope of HIV Gag, SEQ ID NO:28, variable region underlined), WMKSLRVLLVILWLQLSWVWSQQKEVEQNSGPLSVPEGAIASLNCTYSDR
GSQSFFWYRQYSGKSPELIMSIYSNGDKEDGRFTAQLNKASQYVSLLIRD
SQPSDSATYLCAVISNSGNTPLVFGKGTRLSVIANIQNPDPAVYQLRDSK
SSDKSVCLFTDFDSQTNVSQSKDSDVYITDKCVLDMRSMDFKSNSAVAWS
NKSDFACANAFNNSIIPEDTFFPSPESSCDVKLVEKSFETDTNLNFQNLS
VIGFRILLLKVAGFNLLMTLRLWSS (a TCR α subunit for the SL9 epitope of HIV Gag, SEQ ID NO:29, variable region underlined) or WMKSLRVLLVILWLQLSWVWSQQKEVEQNSGPLSVPEGAIASLNCTYSDR
GSQSFFWYRQYSGKSPELIMSIYSNGDKEDGRFTAQLNKASQYVSLLIRD -continued SQPSDSATYLCAVISNSGNTPLVFGKGTRLSVIANIQNPDPAVYQLRDSK
SSDKSVCLFTDFDSQTNVSQSKDSDVYITDKSVLDMRSMDFKSNSAVAWS
NKSDFACANAFNNSIIPEDTFFPSPESSCDVKLVEKSFETDTNLNFQNLS
VIGFRILLLKVAGFNLLMTLRLWSS (a TCR α subunit for the SL9 epitope of HIV Gag, SEQ ID NO:30, variable region underlined) and a second sequence having a 90%, 91%, 92%, 93%, 94%, 95%, 96%, 97%, 98%, 99%, or 100% identity to MGSRLLCWVLLCLLGAGPVKAGVTQTPRYLIKTRGQQVTLSCSPISGHRS
VSWYQQTPGQGLQFLFEYFSETQRNKGNFPGRFSGRQFSNSRSEMNVSTL
ELGDSALYLCASSFDSEQYFGPGTRLTVTEDLKNVFPPEVAVFEPSEAEI
SHTQKATLVCLATGFYPDHVELSWWVNGKEVHSGVCTDPQPLKEQPALND
SRYCLSSRLRVSATFWQNPRNHFRCQVQFYGLSENDEWTQDRAKPVTQIV
SAEAWGRADCGFTSESYQQGVLSATILYEILLGKATLYAVLVSALVLMAM
VKRKDSRG (a TCR β subunit for the SL9 epitope of HIV Gag, SEQ ID NO:31, variable region underlined), MGSRLLCWVLLCLLGAGPVKAGVTQTPRYLIKTRGQQVTLSCSPISGHRS
VSWYQQTPGQGLQFLFEYFSETQRNKGNFPGRFSGRQFSNSRSEMNVSTL
ELGDSALYLCASSFDSEQYFGPGTRLTVTEGLKNVFPPEVAVFEPSEAEI
SHTQKATLVCLATGFYPDHVELSWWVNGKEVHSGVCTDPQPLKEQPALND
SRYCLSSRLRVSATFWQNPRNHFRCQVQFYGLSENDEWTQDRAKPVTQIV
SAEAWGRADCGFTSESYQQGVLSATILYEILLGKATLYAVLVSALVLMAM
VKRKDSRG (a TCR β subunit for the SL9 epitope of HIV Gag, SEQ ID NO:32, variable region underlined), MGSRLLCWVLLCLLGAGPVKAGVTQTPRYLIKTRGQQVTLSCSPISGHRS
VSWYQQTPGQGLQFLFEYFSETQRNKGNFPGRFSGRQFSNSRSEMNVSTL
ELGDSALYLCASSFDSEQYFGPGTRLTVTEGLKNVFPPEVAVFEPSEAEI
SHTQKATLVCLATGFYPDYVELSWWVNGKEVHSGVCTDPQPLKEQPALND
SRYCLSSRLRVSATFWQNPRNHFRCQVQFYGLSENDEWTQDRAKPVTQIV
SAEAWGRADCGFTSESYQQGVLSATILYEILLGKATLYAVLVSALVLMAM
VKRKDSRG (a TCR β subunit for the SL9 epitope of HIV Gag, SEQ ID NO:33, variable region underlined), or MGSRLLCWVLLCLLGAGPVKAGVTQTPRYLIKTRGQQVTLSCSPISGHRS
VSWYQQTPGQGLQFLFEYFSETQRNKGNFPGRFSGRQFSNSRSEMNVSTL
ELGDSALYLCASSFDSEQYFGPGTRLTVTEGLKNVFPPEVAVFEPSEAEI
SHTQKATLVCLATGFYPDYVELSWWVNGKEVHSGVSTDPQPLKEQPALND -continued

SRYCLSSRLRVSATFWQNPRNHFRCQVQFYGLSENDEWTQDRAKPVTQIV

SAEAWGRADCGFTSESYQQGVLSATILYEILLGKATLYAVLVSALVLMAM

VKRKDSRG (a TCR β subunit for the SL9 epitope of HIV Gag, SEQ ID NO:34, variable region underlined).

In preferred embodiments of the present invention, the polypeptide comprises a first sequence that has 98-100%, preferably 99-100%, identity to the variable region (underlined) of one of the first sequences indicated above and a second sequence that has 98-100%, preferably 99-100%, identity to the variable region (underlined) of one of the second sequences indicated above. For example, a polypeptide according to the present invention may comprise a first sequence having 100% identity to the variable region of SEQ ID NO:7, meaning that portions of the first sequence which correspond to the non-underlined portions of SEQ ID NO:7 can have less than 90% identity thereto. In some embodiments, the first sequence, the second sequence, or both, may have 98-100%, preferably 99-100%, identity to the variable regions provided above.

In some embodiments, the present invention provides a nucleic acid molecule (or its complement) which encodes a polypeptide comprising, consisting essentially of, or consisting of a first sequence having a 90%, 91%, 92%, 93%, 94%, 95%, 96%, 97%, 98%, 99%, or 100% identity to SEQ ID NO:7 and a second sequence having a 90%, 91%, 92%, 93%, 94%, 95%, 96%, 97%, 98%, 99%, or 100% identity to SEQ ID NO:8;

a first sequence having a 90%, 91%, 92%, 93%, 94%, 95%, 96%, 97%, 98%, 99%, or 100% identity to SEQ ID NO:9 and a second sequence having a 90%, 91%, 92%, 93%, 94%, 95%, 96%, 97%, 98%, 99%, or 100% identity to SEQ ID NO:10;

a first sequence having a 90%, 91%, 92%, 93%, 94%, 95%, 96%, 97%, 98%, 99%, or 100% identity to SEQ ID NO:11 or SEQ ID NO:12 and a second sequence having a 90%, 91%, 92%, 93%, 94%, 95%, 96%, 97%, 98%, 99%, or 100% identity to SEQ ID NO:13;

a first sequence having a 90%, 91%, 92%, 93%, 94%, 95%, 96%, 97%, 98%, 99%, or 100% identity to SEQ ID NO:14 and a second sequence having a 90%, 91%, 92%, 93%, 94%, 95%, 96%, 97%, 98%, 99%, or 100% identity to SEQ ID NO:15 or SEQ ID NO:16;

a first sequence having a 90%, 91%, 92%, 93%, 94%, 95%, 96%, 97%, 98%, 99%, or 100% identity to SEQ ID NO:17 and a second sequence having a 90%, 91%, 92%, 93%, 94%, 95%, 96%, 97%, 98%, 99%, or 100% identity to SEQ ID NO:18;

a first sequence having a 90%, 91%, 92%, 93%, 94%, 95%, 96%, 97%, 98%, 99%, or 100% identity to SEQ ID NO:19 and a second sequence having a 90%, 91%, 92%, 93%, 94%, 95%, 96%, 97%, 98%, 99%, or 100% identity to SEQ ID NO:20;

a first sequence having a 90%, 91%, 92%, 93%, 94%, 95%, 96%, 97%, 98%, 99%, or 100% identity to SEQ ID NO:21 and a second sequence having a 90%, 91%, 92%, 93%, 94%, 95%, 96%, 97%, 98%, 99%, or 100% identity to SEQ ID NO:22;

a first sequence having a 90%, 91%, 92%, 93%, 94%, 95%, 96%, 97%, 98%, 99%, or 100% identity to SEQ ID NO:23 and a second sequence having a 90%, 91%, 92%, 93%, 94%, 95%, 96%, 97%, 98%, 99%, or 100% identity to SEQ ID NO:24;

a first sequence having a 90%, 91%, 92%, 93%, 94%, 95%, 96%, 97%, 98%, 99%, or 100% identity to SEQ ID NO:25 or SEQ ID NO:26 and a second sequence having a 90%, 91%, 92%, 93%, 94%, 95%, 96%, 97%, 98%, 99%, or 100% identity to SEQ ID NO:27; or a first sequence having a 90%, 91%, 92%, 93%, 94%, 95%, 96%, 97%, 98%, 99%, or 100% identity to SEQ ID NO:28; SEQ ID NO:29; or SEQ ID NO:30 and a second sequence having a 90%, 91%, 92%, 93%, 94%, 95%, 96%, 97%, 98%, 99%, or 100% identity to SEQ ID NO:31; SEQ ID NO:32; SEQ ID NO:33; or SEQ ID NO:34.

In some embodiments, the first sequence (amino acid sequence or nucleotide sequence) and the second sequence (amino acid sequence or nucleotide sequence) need not be directly linked to each other and/or in any particular order. For example, (1) one or more intervening molecules (e.g. amino acid residues or nucleotides) may be located between the first sequence (amino acid sequence or nucleotide sequence) and the second sequence (amino acid sequence or nucleotide sequence), and/or (2) first sequence (amino acid sequence or nucleotide sequence) may be located before or the second sequence (amino acid sequence or nucleotide sequence).

A first sequence having a given percent (%) sequence identity with respect to a second sequence is defined as the percentage of amino acid residues (or nucleotide bases) in the first sequence that are identical with the amino acid residues (or nucleotide bases) in the second sequence, after aligning the first and second sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as ALIGN, ALIGN-2, Megalign (DNASTAR) or BLAST (e.g., Blast, Blast-2, WU-Blast-2) software. Those skilled in the art can determine appropriate parameters for measuring alignment, including any algorithms needed to achieve maximal alignment over the full length of the sequences being compared. For example, the % identity values used herein are generated using WU-BLAST-2 (Altschul et al., *Methods in Enzymology* 266: 460-480 (1996). Most of the WU-BLAST-2 search parameters are set to the default values. For purposes herein, the default parameters of the BLAST alignment tools available online at blast.ncbi.nlm.nih.gov/Blast.cgi were used.

In some embodiments, the polypeptides and/or the nucleic acid molecules according to the present invention are isolated and/or purified. An "isolated" nucleic acid molecule or polypeptide refers to a nucleic acid molecule or polypeptide that is in an environment that is different from its native environment in which the nucleic acid molecule or polypeptide naturally occurs. Isolated nucleic acid molecules or polypeptides includes those having nucleotides or amino acids flanking at least one end that is not native to the given nucleic acid molecule or polypeptide. For example, a promoter P for a protein X is inserted at the 5' end of a protein Y which does not natively have P at its 5' end. Protein Y is thus considered to be "isolated". As used herein, a "purified" polypeptide or nucleic acid molecule means that some or all of the components in the composition from which the polypeptide or the nucleic acid molecule was obtained have been removed.

In some embodiments, the present invention provides recombinant human progenitor cells, engineered human thymocytes, and engineered human T cells which express one or more TCRs clones as disclosed herein.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of producing an engineered thymocyte or an engineered T cell which comprises
   - spectratyping-based cloning to obtain a nucleic acid molecule which encodes a human T cell receptor specific for a virus or an epitope thereof;
   - transducing a human hematopoietic stem cell with a vector containing the nucleic acid molecule to give a recombinant progenitor cell; and
   - differentiating or developing the recombinant progenitor cell into the engineered thymocyte by subjecting the recombinant progenitor cell to a thymus tissue, and then optionally maturing the engineered thymocyte into the engineered T cell, and
   - wherein the spectratyping-based cloning comprises
   - obtaining peripheral blood mononuclear cells from a subject infected with the virus and dividing the peripheral blood mononuclear cells into a first portion and a second portion;
   - culturing the first portion with the virus or the epitope thereof;
   - spectratyping the TCR α-genes and TCR β-genes in the first portion to obtain a first fingerprint;
   - spectratyping the TCR α-genes and TCR β-genes in the second portion to obtain a second fingerprint;
   - selecting a TCR α-gene and a TCR β-gene in the first portion which are not present in the second portion; and
   - recombinantly joining the selected TCR α-gene and TCR β-gene to give the nucleic acid molecule.

2. The method of claim 1, wherein the thymus tissue is human thymus tissue.

3. The method of claim 2, wherein the recombinant progenitor cell is implanted in the human thymus tissue of a subject or intravenously administered to the subject having the human thymus tissue.

4. The method of claim 1, and further comprising activating the engineered T cell by subjecting the engineered T cell to an HLA molecule specific for the human T cell receptor.

5. The method of claim 4, wherein the HLA molecule is HLA-A*0201, HLA-B*39, HLA-A*02, or HLA-B*40.

6. An engineered thymocyte or the engineered T cell made by the method of claim 1.

7. The engineered thymocyte or the engineered T cell of claim 6, which expresses a functional human T cell receptor.

8. The engineered T cell made by the method of claim 1, wherein the engineered T cell is a cytotoxic T cell.

9. The method of claim 1, wherein the nucleic acid molecule encodes a polypeptide comprising
   - a) a first sequence having a 90%, 91%, 92%, 93%, 94%, 95%, 96%, 97%, 98%, 99%, or 100% identity to the variable region of SEQ ID NO:7 and a second sequence having a 90%, 91%, 92%, 93%, 94%, 95%, 96%, 97%, 98%, 99%, or 100% identity to the variable region of SEQ ID NO:8;
   - b) a first sequence having a 90%, 91%, 92%, 93%, 94%, 95%, 96%, 97%, 98%, 99%, or 100% identity to the variable region of SEQ ID NO:9 and a second sequence having a 90%, 91%, 92%, 93%, 94%, 95%, 96%, 97%, 98%, 99%, or 100% identity to the variable region of SEQ ID NO:10;
   - c) a first sequence having a 90%, 91%, 92%, 93%, 94%, 95%, 96%, 97%, 98%, 99%, or 100% identity to the variable region of SEQ ID NO:11 or SEQ ID NO:12 and a second sequence having a 90%, 91%, 92%, 93%, 94%, 95%, 96%, 97%, 98%, 99%, or 100% identity to the variable region of SEQ ID NO:13;
   - d) a first sequence having a 90%, 91%, 92%, 93%, 94%, 95%, 96%, 97%, 98%, 99%, or 100% identity to the variable region of SEQ ID NO:14 and a second sequence having a 90%, 91%, 92%, 93%, 94%, 95%, 96%, 97%, 98%, 99%, or 100% identity to the variable region of SEQ ID NO:15 or SEQ ID NO:16;

e) a first sequence having a 90%, 91%, 92%, 93%, 94%, 95%, 96%, 97%, 98%, 99%, or 100% identity to the variable region of SEQ ID NO:17 and a second sequence having a 90%, 91%, 92%, 93%, 94%, 95%, 96%, 97%, 98%, 99%, or 100% identity to the variable region of SEQ ID NO:18;

f) a first sequence having a 90%, 91%, 92%, 93%, 94%, 95%, 96%, 97%, 98%, 99%, or 100% identity to the variable region of SEQ ID NO:19 and a second sequence having a 90%, 91%, 92%, 93%, 94%, 95%, 96%, 97%, 98%, 99%, or 100% identity to the variable region of SEQ ID NO:20;

g) a first sequence having a 90%, 91%, 92%, 93%, 94%, 95%, 96%, 97%, 98%, 99%, or 100% identity to the variable region of SEQ ID NO:21 and a second sequence having a 90%, 91%, 92%, 93%, 94%, 95%, 96%, 97%, 98%, 99%, or 100% identity to the variable region of SEQ ID NO:22;

h) a first sequence having a 90%, 91%, 92%, 93%, 94%, 95%, 96%, 97%, 98%, 99%, or 100% identity to the variable region of SEQ ID NO:23 and a second sequence having a 90%, 91%, 92%, 93%, 94%, 95%, 96%, 97%, 98%, 99%, or 100% identity to the variable region of SEQ ID NO:24;

i) a first sequence having a 90%, 91%, 92%, 93%, 94%, 95%, 96%, 97%, 98%, 99%, or 100% identity to the variable region of SEQ ID NO:25 or SEQ ID NO:26 and a second sequence having a 90%, 91%, 92%, 93%, 94%, 95%, 96%, 97%, 98%, 99%, or 100% identity to the variable region of SEQ ID NO:27; or j) a first sequence having a 90%, 91%, 92%, 93%, 94%, 95%, 96%, 97%, 98%, 99%, or 100% identity to the variable region of SEQ ID NO:28; SEQ ID NO:29; or SEQ ID NO:30 and a second sequence having a 90%, 91%, 92%, 93%, 94%, 95%, 96%, 97%, 98%, 99%, or 100% identity to the variable region of SEQ ID NO:31; SEQ ID NO:32; SEQ ID NO:33; or SEQ ID NO:34.

10. The method of claim 1, wherein the virus is human immunodeficiency virus or influenza virus.

11. The method of claim 1, wherein the epitope comprises SEQ ID NO:1; SEQ ID NO:2; SEQ ID NO:3; SEQ ID NO:4; SEQ ID NO:5; or SEQ ID NO:6.

12. The method of claim 1, wherein the step of subjecting the recombinant progenitor cell to the thymus tissue is by administering the recombinant progenitor cell to a subject having the thymus tissue.

* * * * *

```
                         SEQUENCE LISTING


<160> NUMBER OF SEQ ID NOS: 39

<210> SEQ ID NO 1
<211> LENGTH: 9
<212> TYPE: PRT
<213> ORGANISM: Human immunodeficiency virus

<400> SEQUENCE: 1

Ser Leu Tyr Asn Thr Val Ala Thr Leu
1               5


<210> SEQ ID NO 2
<211> LENGTH: 11
<212> TYPE: PRT
<213> ORGANISM: Human immunodeficiency virus

<400> SEQUENCE: 2

Gly His Gln Ala Ala Met Gln Met Leu Lys Glu
1               5                   10


<210> SEQ ID NO 3
<211> LENGTH: 9
<212> TYPE: PRT
<213> ORGANISM: Human immunodeficiency virus

<400> SEQUENCE: 3

Ala Ile Ile Arg Ile Leu Gln Gln Leu
1               5


<210> SEQ ID NO 4
<211> LENGTH: 9
<212> TYPE: PRT
<213> ORGANISM: Human immunodeficiency virus

<400> SEQUENCE: 4

Arg Ile Leu Gln Gln Leu Leu Phe Ile
1               5


<210> SEQ ID NO 5
<211> LENGTH: 9
<212> TYPE: PRT
<213> ORGANISM: Human immunodeficiency virus

<400> SEQUENCE: 5

Ala Phe His His Met Ala Arg Glu Leu
1               5


<210> SEQ ID NO 6
<211> LENGTH: 10
<212> TYPE: PRT
<213> ORGANISM: Human immunodeficiency virus

<400> SEQUENCE: 6

Gln Glu Leu Lys Asn Ser Ala Val Ser Leu
1               5                   10
```

<210> SEQ ID NO 7
<211> LENGTH: 275
<212> TYPE: PRT
<213> ORGANISM: Homo sapiens

<400> SEQUENCE: 7

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Ile Ser Asn Ser Gly Asn Thr Pro Leu Val Phe Gly Lys Gly Thr
        115                 120                 125

Arg Leu Ser Val Ile Ala Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275
```

<210> SEQ ID NO 8
<211> LENGTH: 308
<212> TYPE: PRT
<213> ORGANISM: Homo sapiens

<400> SEQUENCE: 8

```
Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45
```

```
Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Phe Asp Ser Glu Gln Tyr Phe Gly Pro Gly Thr Arg Leu Thr Val
        115                 120                 125

Thr Glu Asp Leu Lys Asn Val Phe Pro Pro Glu Val Ala Val Phe Glu
    130                 135                 140

Pro Ser Glu Ala Glu Ile Ser His Thr Gln Lys Ala Thr Leu Val Cys
145                 150                 155                 160

Leu Ala Thr Gly Phe Tyr Pro Asp His Val Glu Leu Ser Trp Trp Val
                165                 170                 175

Asn Gly Lys Glu Val His Ser Gly Val Cys Thr Asp Pro Gln Pro Leu
            180                 185                 190

Lys Glu Gln Pro Ala Leu Asn Asp Ser Arg Tyr Cys Leu Ser Ser Arg
        195                 200                 205

Leu Arg Val Ser Ala Thr Phe Trp Gln Asn Pro Arg Asn His Phe Arg
    210                 215                 220

Cys Gln Val Gln Phe Tyr Gly Leu Ser Glu Asn Asp Glu Trp Thr Gln
225                 230                 235                 240

Asp Arg Ala Lys Pro Val Thr Gln Ile Val Ser Ala Glu Ala Trp Gly
                245                 250                 255

Arg Ala Asp Cys Gly Phe Thr Ser Glu Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Ala Leu Val Leu Met Ala Met Val Lys Arg Lys
    290                 295                 300

Asp Ser Arg Gly
305


<210> SEQ ID NO 9
<211> LENGTH: 251
<212> TYPE: PRT
<213> ORGANISM: Homo sapiens

<400> SEQUENCE: 9

Met Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Ala Gly Ser Gln Gly
                85                  90                  95

Asn Leu Ile Phe Gly Lys Gly Thr Lys Leu Ser Val Lys Pro Asn Ile
```

```
            100                 105                 110

Gln Asn Pro Asp Pro Ala Val Tyr Gln Leu Arg Asp Ser Lys Ser Ser
        115                 120                 125

Asp Lys Ser Val Cys Leu Phe Thr Asp Phe Asp Ser Gln Thr Asn Val
    130                 135                 140

Ser Gln Ser Lys Asp Ser Asp Val Tyr Ile Thr Asp Lys Thr Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser Cys Asp Val Lys
        195                 200                 205

Leu Val Glu Lys Ser Phe Glu Thr Asp Thr Asn Leu Asn Phe Gln Asn
    210                 215                 220

Leu Ser Val Ile Gly Phe Arg Ile Leu Leu Leu Lys Val Ala Gly Phe
225                 230                 235                 240

Asn Leu Leu Met Thr Leu Arg Leu Trp Ser Ser
                245                 250


<210> SEQ ID NO 10
<211> LENGTH: 292
<212> TYPE: PRT
<213> ORGANISM: Homo sapiens

<400> SEQUENCE: 10

Met Val Asp Gly Gly Ile Thr Gln Ser Pro Lys Tyr Leu Phe Arg Lys
1               5                   10                  15

Glu Gly Gln Asn Val Thr Leu Ser Cys Glu Gln Asn Leu Asn His Asp
            20                  25                  30

Ala Met Tyr Trp Tyr Arg Gln Asp Pro Gly Gln Gly Leu Arg Leu Ile
        35                  40                  45

Tyr Tyr Ser Gln Ile Val Asn Asp Phe Gln Lys Gly Asp Ile Ala Glu
    50                  55                  60

Gly Tyr Ser Val Ser Arg Glu Lys Lys Glu Ser Phe Pro Leu Thr Val
65                  70                  75                  80

Thr Ser Ala Gln Lys Asn Pro Thr Ala Phe Tyr Leu Cys Ala Ser Ser
                85                  90                  95

Ser Arg Ser Ser Tyr Glu Gln Tyr Phe Gly Pro Gly Thr Arg Leu Thr
            100                 105                 110

Val Thr Glu Asp Leu Lys Asn Val Phe Pro Pro Glu Val Ala Val Phe
        115                 120                 125

Glu Pro Ser Glu Ala Glu Ile Ser His Thr Gln Lys Ala Thr Leu Val
    130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Ser Thr Asp Pro Gln Pro
                165                 170                 175

Leu Lys Glu Gln Pro Ala Leu Asn Asp Ser Arg Tyr Ser Leu Ser Ser
            180                 185                 190

Arg Leu Arg Val Ser Ala Thr Phe Trp Gln Asn Pro Arg Asn His Phe
        195                 200                 205

Arg Cys Gln Val Gln Phe Tyr Gly Leu Ser Glu Asn Asp Glu Trp Thr
    210                 215                 220
```

```
Gln Asp Arg Ala Lys Pro Val Thr Gln Ile Val Ser Ala Glu Ala Trp
225                 230                 235                 240

Gly Arg Ala Asp Cys Gly Phe Thr Ser Glu Ser Tyr Gln Gln Gly Val
                245                 250                 255

Leu Ser Ala Thr Ile Leu Tyr Glu Ile Leu Leu Gly Lys Ala Thr Leu
            260                 265                 270

Tyr Ala Val Leu Val Ser Ala Leu Val Leu Met Ala Met Gln Glu Lys
        275                 280                 285

Gly Phe Gln Arg
    290


<210> SEQ ID NO 11
<211> LENGTH: 270
<212> TYPE: PRT
<213> ORGANISM: Homo sapiens

<400> SEQUENCE: 11

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Ser Val Phe Ser
        35                  40                  45

Ser Leu Gln Trp Tyr Arg Gln Glu Pro Gly Glu Gly Pro Val Leu Leu
    50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
                85                  90                  95

Ala Gln Pro Gly Asp Thr Gly Leu Tyr Leu Cys Ala Gly Ala Gly Trp
            100                 105                 110

Arg Asp Asp Lys Ile Ile Phe Gly Lys Gly Thr Arg Leu His Ile Leu
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Ala Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270


<210> SEQ ID NO 12
<211> LENGTH: 280
<212> TYPE: PRT
<213> ORGANISM: Homo sapiens
```

<400> SEQUENCE: 12

```
Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Asn Ser Leu Asp Arg Asp Asp Lys Ile Ile
        115                 120                 125

Phe Gly Lys Gly Thr Arg Leu His Ile Leu Pro Asn Ile Gln Asn Pro
    130                 135                 140

Asp Pro Ala Val Tyr Gln Leu Arg Asp Ser Lys Ser Ser Asp Lys Ser
145                 150                 155                 160

Val Cys Leu Phe Thr Asp Phe Asp Ser Gln Thr Asn Val Ser Gln Ser
                165                 170                 175

Lys Asp Ser Asp Val Tyr Ile Thr Asp Lys Thr Val Leu Asp Met Arg
            180                 185                 190

Ser Met Asp Phe Lys Ser Asn Ser Ala Val Ala Trp Ser Asn Lys Ser
        195                 200                 205

Asp Phe Ala Cys Ala Asn Ala Phe Asn Asn Ser Ile Ile Pro Ala Asp
    210                 215                 220

Thr Phe Phe Pro Ser Pro Glu Ser Ser Cys Asp Val Lys Leu Val Glu
225                 230                 235                 240

Lys Ser Phe Glu Thr Asp Thr Asn Leu Asn Phe Gln Asn Leu Ser Val
                245                 250                 255

Ile Gly Phe Arg Ile Leu Leu Leu Lys Val Ala Gly Phe Asn Leu Leu
            260                 265                 270

Met Thr Leu Arg Leu Trp Ser Ser
        275                 280
```

<210> SEQ ID NO 13
<211> LENGTH: 305
<212> TYPE: PRT
<213> ORGANISM: Homo sapiens

<400> SEQUENCE: 13

```
Met Leu Ser Leu Leu Leu Leu Leu Leu Gly Leu Ser Val Phe Ser Ala
1               5                   10                  15

Val Ile Ser Gln Lys Pro Ser Arg Asp Ile Cys Gln Arg Gly Thr Ser
            20                  25                  30

Leu Thr Ile Gln Cys Gln Val Asp Ser Gln Val Thr Met Met Phe Trp
        35                  40                  45

Tyr Arg Gln Gln Pro Gly Gln Ser Leu Thr Leu Ile Ala Thr Ala Asn
    50                  55                  60

Gln Gly Ser Glu Ala Thr Tyr Glu Ser Gly Phe Val Ile Asp Lys Phe
65                  70                  75                  80
```

```
Pro Ile Ser Arg Pro Asn Leu Thr Phe Ser Thr Leu Thr Val Ser Asn
                85                  90                  95

Met Ser Pro Glu Asp Ser Ser Ile Tyr Leu Cys Ser Val Gly Pro Arg
            100                 105                 110

Gln Gly Gly Glu Gln Tyr Phe Gly Pro Gly Thr Arg Leu Thr Val Thr
        115                 120                 125

Glu Asp Leu Asn Lys Val Phe Pro Pro Glu Val Ala Val Phe Glu Pro
    130                 135                 140

Ser Glu Ala Glu Ile Ser His Thr Gln Lys Ala Thr Leu Val Cys Leu
145                 150                 155                 160

Ala Thr Gly Phe Phe Pro Asp His Val Glu Leu Ser Trp Trp Val Asn
                165                 170                 175

Gly Lys Glu Val His Ser Gly Val Ser Thr Asp Pro Gln Pro Leu Lys
            180                 185                 190

Glu Gln Pro Ala Leu Asn Asp Ser Arg Tyr Cys Leu Ser Ser Arg Leu
        195                 200                 205

Arg Val Ser Ala Thr Phe Trp Gln Asn Pro Arg Asn His Phe Arg Cys
    210                 215                 220

Gln Val Gln Phe Tyr Gly Leu Ser Glu Asn Asp Glu Trp Thr Gln Asp
225                 230                 235                 240

Arg Ala Lys Pro Val Thr Gln Ile Val Ser Ala Glu Ala Trp Gly Arg
                245                 250                 255

Ala Asp Cys Gly Phe Thr Ser Val Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Ala Leu Val Leu Met Ala Met Val Lys Arg Lys Asp
    290                 295                 300

Phe
305


<210> SEQ ID NO 14
<211> LENGTH: 273
<212> TYPE: PRT
<213> ORGANISM: Homo sapiens

<400> SEQUENCE: 14

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
            20                  25                  30

Glu Pro Val His Leu Pro Cys Asn His Ser Thr Ile Ser Gly Thr Asp
        35                  40                  45

Tyr Ile His Trp Tyr Arg Gln Leu Pro Ser Gln Gly Pro Glu Tyr Val
    50                  55                  60

Ile His Gly Leu Thr Ser Asn Val Asn Asn Arg Met Ala Ser Leu Ala
65                  70                  75                  80

Ile Ala Glu Asp Arg Lys Ser Ser Thr Leu Ile Leu His Arg Ala Thr
                85                  90                  95

Leu Arg Asp Ala Ala Val Tyr Tyr Cys Ile Leu Ile Pro Pro Pro Tyr
            100                 105                 110

Ser Gly Ala Gly Ser Tyr Gln Leu Thr Phe Gly Lys Gly Thr Lys Leu
        115                 120                 125

Ser Val Ile Pro Asn Ile Gln Asn Pro Asp Pro Ala Val Tyr Gln Leu
```

```
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Ala Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser


<210> SEQ ID NO 15
<211> LENGTH: 320
<212> TYPE: PRT
<213> ORGANISM: Homo sapiens

<400> SEQUENCE: 15

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Ser Leu Arg Ala Ala
        115                 120                 125

Ser Tyr Gly Tyr Thr Phe Gly Ser Gly Thr Arg Leu Thr Val Val Glu
    130                 135                 140

Asp Leu Asn Lys Val Phe Pro Pro Glu Val Ala Val Phe Glu Pro Ser
145                 150                 155                 160

Glu Ala Glu Ile Ser His Thr Gln Lys Ala Thr Leu Val Cys Leu Ala
                165                 170                 175

Thr Gly Phe Phe Pro Asp His Val Glu Leu Ser Trp Trp Val Asn Gly
            180                 185                 190

Lys Glu Val His Ser Gly Val Ser Thr Asp Pro Gln Pro Leu Lys Glu
        195                 200                 205

Gln Pro Ala Leu Asn Asp Ser Arg Tyr Cys Leu Ser Ser Arg Leu Arg
    210                 215                 220

Val Ser Ala Thr Phe Trp Gln Asn Pro Arg Asn His Phe Arg Cys Gln
```

```
225                 230                 235                 240

Val Gln Phe Tyr Gly Leu Ser Glu Asn Asp Glu Trp Thr Gln Asp Arg
                245                 250                 255

Ala Lys Pro Val Thr Gln Ile Val Ser Ala Glu Ala Trp Gly Arg Ala
            260                 265                 270

Asp Cys Gly Phe Thr Ser Val Ser Tyr Gln Gln Gly Val Leu Ser Ala
        275                 280                 285

Thr Ile Leu Tyr Glu Ile Leu Leu Gly Lys Ala Thr Leu Tyr Ala Val
    290                 295                 300

Leu Val Ser Ala Leu Val Leu Met Ala Met Val Lys Arg Lys Asp Phe
305                 310                 315                 320


<210> SEQ ID NO 16
<211> LENGTH: 311
<212> TYPE: PRT
<213> ORGANISM: Homo sapiens

<400> SEQUENCE: 16

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Ser Gln Ala Val Ser Thr Asp Thr Gln Tyr Phe Gly Pro Gly
        115                 120                 125

Thr Arg Leu Thr Val Leu Glu Asp Leu Asn Lys Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
        275                 280                 285
```

```
Lys Ala Thr Leu Tyr Ala Val Leu Val Ser Ala Leu Val Leu Met Ala
    290                 295                 300

Met Val Lys Arg Lys Asp Phe
305                 310


<210> SEQ ID NO 17
<211> LENGTH: 273
<212> TYPE: PRT
<213> ORGANISM: Homo sapiens

<400> SEQUENCE: 17

Met Leu Leu Leu Leu Ile Pro Val Leu Gly Met Ile Phe Ala Leu Arg
1               5                   10                  15

Asp Ala Arg Ala Gln Ser Val Ser Gln His Asn His His Val Ile Leu
            20                  25                  30

Ser Glu Ala Ala Ser Leu Glu Leu Gly Cys Asn Tyr Ser Tyr Gly Gly
        35                  40                  45

Thr Val Asn Leu Phe Trp Tyr Val Gln Tyr Pro Gly Gln His Leu Gln
    50                  55                  60

Leu Leu Leu Lys Tyr Phe Ser Gly Asp Pro Leu Val Lys Gly Ile Lys
65                  70                  75                  80

Gly Phe Glu Ala Glu Phe Ile Lys Ser Lys Phe Ser Phe Asn Leu Arg
                85                  90                  95

Lys Pro Ser Val Gln Trp Ser Asp Thr Ala Glu Tyr Phe Cys Ala Val
            100                 105                 110

Ile Glu Asp Ser Ser Tyr Lys Leu Ile Phe Gly Ser Gly Thr Arg Leu
        115                 120                 125

Leu Val Arg Pro Asp Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser


<210> SEQ ID NO 18
<211> LENGTH: 308
<212> TYPE: PRT
<213> ORGANISM: Homo sapiens

<400> SEQUENCE: 18

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
```

```
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Glu His Glu Gln Tyr Phe Gly Pro Gly Thr Arg Leu Thr
        115                 120                 125

Val Thr Glu Asp Leu Lys Asn Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Gln Glu Lys
    290                 295                 300

Gly Phe Gln Arg
305


<210> SEQ ID NO 19
<211> LENGTH: 275
<212> TYPE: PRT
<213> ORGANISM: Homo sapiens

<400> SEQUENCE: 19

Met Leu Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
            20                  25                  30

Ser Glu Gly Ala Leu Val Leu Leu Arg Cys Asn Tyr Ser Ser Ser Val
        35                  40                  45

Pro Pro Tyr Leu Phe Trp Tyr Val Gln Tyr Pro Asn Gln Gly Leu Gln
    50                  55                  60

Leu Leu Leu Lys Tyr Thr Thr Gly Ala Thr Leu Val Lys Gly Ile Asn
65                  70                  75                  80
```

```
Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
            100                 105                 110

Ser Glu Ile Glu Phe Gly Asn Glu Lys Leu Thr Phe Gly Thr Gly Thr
        115                 120                 125

Arg Leu Thr Ile Ile Pro Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275


<210> SEQ ID NO 20
<211> LENGTH: 315
<212> TYPE: PRT
<213> ORGANISM: Homo sapiens

<400> SEQUENCE: 20

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30

Lys Arg Gly Gln Asp Val Ala Leu Arg Cys Asp Pro Ile Ser Gly His
        35                  40                  45

Val Ser Leu Phe Trp Tyr Gln Gln Ala Leu Gly Gln Gly Pro Glu Phe
    50                  55                  60

Leu Thr Tyr Phe Gln Asn Glu Ala Gln Leu Asp Lys Ser Gly Leu Pro
65                  70                  75                  80

Ser Asp Arg Phe Phe Ala Glu Arg Pro Glu Gly Ser Val Ser Thr Leu
                85                  90                  95

Lys Ile Gln Arg Thr Gln Gln Glu Asp Ser Ala Val Tyr Leu Cys Ala
            100                 105                 110

Ser Ser Ala Gly Leu Gly Thr Gly Thr Ser Tyr Glu Gln Tyr Phe Gly
        115                 120                 125

Pro Gly Thr Arg Leu Thr Val Thr Glu Asp Leu Lys Asn Val Phe Pro
    130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Tyr Pro Asp His
                165                 170                 175
```

```
Val Glu Leu Ser Trp Trp Val Asn Gly Lys Glu Val His Ser Gly Val
            180                 185                 190

Cys Thr Asp Pro Gln Pro Leu Lys Glu Gln Pro Ala Leu Asn Asp Ser
        195                 200                 205

Arg Tyr Cys Leu Ser Ser Arg Leu Arg Val Ser Ala Thr Phe Trp Gln
    210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Glu
            260                 265                 270

Ser Tyr Gln Gln Gly Val Leu Ser Ala Thr Ile Leu Tyr Glu Ile Leu
        275                 280                 285

Leu Gly Lys Ala Thr Leu Tyr Ala Val Leu Val Ser Ala Leu Val Leu
    290                 295                 300

Met Ala Met Val Lys Arg Lys Asp Ser Arg Gly
305                 310                 315


<210> SEQ ID NO 21
<211> LENGTH: 282
<212> TYPE: PRT
<213> ORGANISM: Homo sapiens

<400> SEQUENCE: 21

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Pro Phe Leu Ser Thr Gly Ala Asn Ser
        115                 120                 125

Lys Leu Thr Phe Gly Lys Gly Ile Thr Leu Ser Arg Pro Asp Ile Gln
    130                 135                 140

Asn Pro Asp Pro Ala Val Tyr Gln Leu Arg Asp Ser Lys Ser Ser Asp
145                 150                 155                 160

Lys Ser Val Cys Leu Phe Thr Asp Phe Asp Ser Gln Thr Asn Val Ser
                165                 170                 175

Gln Ser Lys Asp Ser Asp Val Tyr Ile Thr Asp Lys Thr Val Leu Asp
            180                 185                 190

Met Arg Ser Met Asp Phe Lys Ser Asn Ser Ala Val Ala Trp Ser Asn
        195                 200                 205

Lys Ser Asp Phe Ala Cys Ala Asn Ala Phe Asn Asn Ser Ile Ile Pro
    210                 215                 220

Glu Asp Thr Phe Phe Pro Ser Pro Glu Ser Ser Cys Asp Val Lys Leu
```

```
225                 230                 235                 240

Val Glu Lys Ser Phe Glu Thr Asp Thr Asn Leu Asn Phe Gln Asn Leu
                245                 250                 255

Ser Val Ile Gly Phe Arg Ile Leu Leu Leu Lys Val Ala Gly Phe Asn
            260                 265                 270

Leu Leu Met Thr Leu Arg Leu Trp Ser Ser
        275                 280


<210> SEQ ID NO 22
<211> LENGTH: 309
<212> TYPE: PRT
<213> ORGANISM: Homo sapiens

<400> SEQUENCE: 22

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Glu His Glu Gln Tyr Phe Gly Pro Gly Thr Arg Leu Thr
        115                 120                 125

Val Thr Glu Asp Leu Lys Asn Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Cys Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Ser Arg Gly
305
```

<210> SEQ ID NO 23
<211> LENGTH: 271
<212> TYPE: PRT
<213> ORGANISM: Homo sapiens

<400> SEQUENCE: 23

```
Met Ala Gly Ile Arg Ala Leu Phe Met Tyr Leu Trp Leu Gln Leu Asp
1               5                   10                  15

Trp Val Ser Arg Gly Glu Ser Val Gly Leu His Leu Pro Thr Leu Ser
            20                  25                  30

Val Gln Glu Gly Asp Asn Ser Ile Ile Asn Cys Ala Tyr Ser Asn Ser
        35                  40                  45

Ala Ser Asp Tyr Phe Ile Trp Tyr Lys Gln Glu Ser Gly Lys Gly Pro
    50                  55                  60

Gln Phe Ile Ile Asp Ile Arg Ser Asn Met Asp Lys Arg Gln Gly Gln
65                  70                  75                  80

Arg Val Thr Val Leu Leu Asn Lys Thr Val Lys His Leu Ser Leu Gln
                85                  90                  95

Ile Ala Ala Thr Gln Pro Gly Asp Ser Ala Val Tyr Phe Cys Ala Glu
            100                 105                 110

Arg Ala Gly Asn Gln Phe Tyr Phe Gly Thr Gly Thr Ser Leu Thr Val
        115                 120                 125

Ile Pro Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270
```

<210> SEQ ID NO 24
<211> LENGTH: 310
<212> TYPE: PRT
<213> ORGANISM: Homo sapiens

<400> SEQUENCE: 24

```
Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60
```

```
Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Lys Ala Gly Gly Met Thr Glu Ala Phe Phe Gly Gln Gly Thr Arg Leu
        115                 120                 125

Thr Val Val Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310


<210> SEQ ID NO 25
<211> LENGTH: 273
<212> TYPE: PRT
<213> ORGANISM: Homo sapiens

<400> SEQUENCE: 25

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Ile Gly Asn Ala Gly Asn Met Leu Thr Phe Gly Gly Gly Thr Arg Leu
        115                 120                 125
```

```
Met Val Lys Pro His Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser


<210> SEQ ID NO 26
<211> LENGTH: 270
<212> TYPE: PRT
<213> ORGANISM: Homo sapiens

<400> SEQUENCE: 26

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Val Ser Asp Gly Gly Leu
            100                 105                 110

Asn Thr Asp Lys Leu Ile Phe Gly Thr Gly Thr Arg Leu Gln Val Phe
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220
```

```
Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270


<210> SEQ ID NO 27
<211> LENGTH: 307
<212> TYPE: PRT
<213> ORGANISM: Homo sapiens

<400> SEQUENCE: 27

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile His Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Ala Leu Glu Thr Pro Tyr Ile Leu Glu Arg Glu Val Gly Ser
        115                 120                 125

Gln Asp Leu Lys Asn Val Phe Pro Pro Glu Val Ala Val Phe Glu Pro
    130                 135                 140

Ser Glu Ala Glu Ile Ser His Thr Gln Lys Ala Thr Leu Val Cys Leu
145                 150                 155                 160

Ala Thr Gly Phe Tyr Pro Asp His Val Glu Leu Ser Trp Trp Val Asn
                165                 170                 175

Gly Lys Glu Val His Ser Gly Val Cys Thr Asp Pro Gln Pro Leu Lys
            180                 185                 190

Glu Gln Pro Ala Leu Asn Asp Ser Arg Tyr Cys Leu Ser Ser Arg Leu
        195                 200                 205

Arg Val Ser Ala Thr Phe Trp Gln Asn Pro Arg Asn His Phe Arg Cys
    210                 215                 220

Gln Val Gln Phe Tyr Gly Leu Ser Glu Asn Asp Glu Trp Thr Gln Asp
225                 230                 235                 240

Arg Ala Lys Pro Val Thr Gln Ile Val Ser Ala Glu Ala Trp Gly Arg
                245                 250                 255

Ala Asp Cys Gly Phe Thr Ser Glu Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Ala Leu Val Leu Met Ala Met Val Lys Arg Lys Asp
    290                 295                 300

Ser Arg Gly
305
```

<210> SEQ ID NO 28
<211> LENGTH: 275
<212> TYPE: PRT
<213> ORGANISM: Homo sapiens

<400> SEQUENCE: 28

```
Leu Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Ile Ser Asn Ser Gly Asn Thr Pro Leu Val Phe Gly Lys Gly Thr
        115                 120                 125

Arg Leu Ser Val Ile Ala Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Cys Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275
```

<210> SEQ ID NO 29
<211> LENGTH: 275
<212> TYPE: PRT
<213> ORGANISM: Homo sapiens

<400> SEQUENCE: 29

```
Trp Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
```

```
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Ile Ser Asn Ser Gly Asn Thr Pro Leu Val Phe Gly Lys Gly Thr
        115                 120                 125

Arg Leu Ser Val Ile Ala Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Cys Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275


<210> SEQ ID NO 30
<211> LENGTH: 275
<212> TYPE: PRT
<213> ORGANISM: Homo sapiens

<400> SEQUENCE: 30

Trp Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Ile Ser Asn Ser Gly Asn Thr Pro Leu Val Phe Gly Lys Gly Thr
        115                 120                 125

Arg Leu Ser Val Ile Ala Asn Ile Gln Asn Pro Asp Pro Ala Val Tyr
    130                 135                 140
```

```
Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Ser Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275


<210> SEQ ID NO 31
<211> LENGTH: 308
<212> TYPE: PRT
<213> ORGANISM: Homo sapiens

<400> SEQUENCE: 31

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Phe Asp Ser Glu Gln Tyr Phe Gly Pro Gly Thr Arg Leu Thr Val
        115                 120                 125

Thr Glu Asp Leu Lys Asn Val Phe Pro Pro Glu Val Ala Val Phe Glu
    130                 135                 140

Pro Ser Glu Ala Glu Ile Ser His Thr Gln Lys Ala Thr Leu Val Cys
145                 150                 155                 160

Leu Ala Thr Gly Phe Tyr Pro Asp His Val Glu Leu Ser Trp Trp Val
                165                 170                 175

Asn Gly Lys Glu Val His Ser Gly Val Cys Thr Asp Pro Gln Pro Leu
            180                 185                 190

Lys Glu Gln Pro Ala Leu Asn Asp Ser Arg Tyr Cys Leu Ser Ser Arg
        195                 200                 205

Leu Arg Val Ser Ala Thr Phe Trp Gln Asn Pro Arg Asn His Phe Arg
    210                 215                 220

Cys Gln Val Gln Phe Tyr Gly Leu Ser Glu Asn Asp Glu Trp Thr Gln
225                 230                 235                 240
```

```
Asp Arg Ala Lys Pro Val Thr Gln Ile Val Ser Ala Glu Ala Trp Gly
                245                 250                 255

Arg Ala Asp Cys Gly Phe Thr Ser Glu Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Ala Leu Val Leu Met Ala Met Val Lys Arg Lys
    290                 295                 300

Asp Ser Arg Gly
305


<210> SEQ ID NO 32
<211> LENGTH: 308
<212> TYPE: PRT
<213> ORGANISM: Homo sapiens

<400> SEQUENCE: 32

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Phe Asp Ser Glu Gln Tyr Phe Gly Pro Gly Thr Arg Leu Thr Val
        115                 120                 125

Thr Glu Gly Leu Lys Asn Val Phe Pro Pro Glu Val Ala Val Phe Glu
    130                 135                 140

Pro Ser Glu Ala Glu Ile Ser His Thr Gln Lys Ala Thr Leu Val Cys
145                 150                 155                 160

Leu Ala Thr Gly Phe Tyr Pro Asp His Val Glu Leu Ser Trp Trp Val
                165                 170                 175

Asn Gly Lys Glu Val His Ser Gly Val Cys Thr Asp Pro Gln Pro Leu
            180                 185                 190

Lys Glu Gln Pro Ala Leu Asn Asp Ser Arg Tyr Cys Leu Ser Ser Arg
        195                 200                 205

Leu Arg Val Ser Ala Thr Phe Trp Gln Asn Pro Arg Asn His Phe Arg
    210                 215                 220

Cys Gln Val Gln Phe Tyr Gly Leu Ser Glu Asn Asp Glu Trp Thr Gln
225                 230                 235                 240

Asp Arg Ala Lys Pro Val Thr Gln Ile Val Ser Ala Glu Ala Trp Gly
                245                 250                 255

Arg Ala Asp Cys Gly Phe Thr Ser Glu Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Ala Leu Val Leu Met Ala Met Val Lys Arg Lys
```

```
    290                 295                 300

Asp Ser Arg Gly
305


<210> SEQ ID NO 33
<211> LENGTH: 308
<212> TYPE: PRT
<213> ORGANISM: Homo sapiens

<400> SEQUENCE: 33

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Phe Asp Ser Glu Gln Tyr Phe Gly Pro Gly Thr Arg Leu Thr Val
        115                 120                 125

Thr Glu Gly Leu Lys Asn Val Phe Pro Pro Glu Val Ala Val Phe Glu
    130                 135                 140

Pro Ser Glu Ala Glu Ile Ser His Thr Gln Lys Ala Thr Leu Val Cys
145                 150                 155                 160

Leu Ala Thr Gly Phe Tyr Pro Asp Tyr Val Glu Leu Ser Trp Trp Val
                165                 170                 175

Asn Gly Lys Glu Val His Ser Gly Val Cys Thr Asp Pro Gln Pro Leu
            180                 185                 190

Lys Glu Gln Pro Ala Leu Asn Asp Ser Arg Tyr Cys Leu Ser Ser Arg
        195                 200                 205

Leu Arg Val Ser Ala Thr Phe Trp Gln Asn Pro Arg Asn His Phe Arg
    210                 215                 220

Cys Gln Val Gln Phe Tyr Gly Leu Ser Glu Asn Asp Glu Trp Thr Gln
225                 230                 235                 240

Asp Arg Ala Lys Pro Val Thr Gln Ile Val Ser Ala Glu Ala Trp Gly
                245                 250                 255

Arg Ala Asp Cys Gly Phe Thr Ser Glu Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Ala Leu Val Leu Met Ala Met Val Lys Arg Lys
    290                 295                 300

Asp Ser Arg Gly
305


<210> SEQ ID NO 34
<211> LENGTH: 308
<212> TYPE: PRT
<213> ORGANISM: Homo sapiens
```

<400> SEQUENCE: 34

```
Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Phe Asp Ser Glu Gln Tyr Phe Gly Pro Gly Thr Arg Leu Thr Val
        115                 120                 125

Thr Glu Gly Leu Lys Asn Val Phe Pro Pro Glu Val Ala Val Phe Glu
    130                 135                 140

Pro Ser Glu Ala Glu Ile Ser His Thr Gln Lys Ala Thr Leu Val Cys
145                 150                 155                 160

Leu Ala Thr Gly Phe Tyr Pro Asp Tyr Val Glu Leu Ser Trp Trp Val
                165                 170                 175

Asn Gly Lys Glu Val His Ser Gly Val Ser Thr Asp Pro Gln Pro Leu
            180                 185                 190

Lys Glu Gln Pro Ala Leu Asn Asp Ser Arg Tyr Cys Leu Ser Ser Arg
        195                 200                 205

Leu Arg Val Ser Ala Thr Phe Trp Gln Asn Pro Arg Asn His Phe Arg
    210                 215                 220

Cys Gln Val Gln Phe Tyr Gly Leu Ser Glu Asn Asp Glu Trp Thr Gln
225                 230                 235                 240

Asp Arg Ala Lys Pro Val Thr Gln Ile Val Ser Ala Glu Ala Trp Gly
                245                 250                 255

Arg Ala Asp Cys Gly Phe Thr Ser Glu Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Ala Leu Val Leu Met Ala Met Val Lys Arg Lys
    290                 295                 300

Asp Ser Arg Gly
305
```

<210> SEQ ID NO 35
<211> LENGTH: 1833
<212> TYPE: DNA
<213> ORGANISM: Homo sapiens

<400> SEQUENCE: 35

```
ggatccgcca ccatgaaatc cttgagagtt ttactagtga tcctgtggct tcagttgagc      60

tgggtttgga gccaacagaa ggaggtggag cagaattctg gacccctcag tgttccagag     120

ggagccattg cctctctcaa ctgcacttac agtgaccgag gttcccagtc cttcttctgg     180

tacagacaat attctgggaa aagccctgag ttgataatgt ccatatactc caatggtgac     240

aaagaagatg gaaggtttac agcacagctc aataaagcca gccagtatgt ttctctgctc     300
```

```
atcagagact cccagcccag tgattcagcc acctacctct gtgccgtgat ctccaattca    360

ggaaacacac ctcttgtctt tggaaagggc acaagacttt ctgtgattgc aaatatccag    420

aaccctgacc ctgccgtgta ccagctgaga gactctaaat ccagtgacaa gtctgtctgc    480

ctattcaccg attttgattc tcaaacaaat gtgtcacaaa gtaaggattc tgatgtgtat    540

atcacagaca aaactgtgct agacatgagg tctatggact tcaagagcaa cagtgctgtg    600

gcctggagca acaaatctga ctttgcatgt gcaaacgcct tcaacaacag cattattcca    660

gaagacacct tcttccccag cccagaaagt tcctgtgatg tcaagctggt cgagaaaagc    720

tttgaaacag atacgaacct aaactttcaa aacctgtcag tgattgggtt ccgaatcctc    780

ctcctgaaag tggccgggtt taatctgctc atgacgctgc ggctgtggtc cagcggttcc    840

ggagccacga acttctctct gttaaagcaa gcaggagacg tggaagaaaa ccccggtccc    900

atgggctcca ggctgctctg ttgggtgctg ctttgtctcc tgggagcagg cccagtaaag    960

gctggagtca ctcaaactcc aagatatctg atcaaaacga gaggacagca agtgacactg   1020

agctgctccc ctatctctgg gcataggagt gtatcctggt accaacagac cccaggacag   1080

ggccttcagt tcctctttga atacttcagt gagacacaga gaaacaaagg aaacttccct   1140

ggtcgattct cagggcgcca gttctctaac tctcgctctg agatgaatgt gagcaccttg   1200

gagctggggg actcggccct ttatctttgc gccagcagct ttgactctga gcagtacttc   1260

gggccgggca ccaggctcac ggtcacagag gacctgaaaa acgtgttccc acccgaggtc   1320

gctgtgtttg agccatcaga agcagagatc tcccacaccc aaaaggccac actggtgtgc   1380

ctggccacag gcttctaccc cgaccacgtg gagctgagct ggtgggtgaa tgggaaggag   1440

gtgcacagtg ggtcagcac agacccgcag cccctcaagg agcagcccgc cctcaatgac    1500

tccagatact gcctgagcag ccgcctgagg gtctcggcca ccttctggca gaacccccgc   1560

aaccacttcc gctgtcaagt ccagttctac gggctctcgg agaatgacga gtggacccag   1620

gatagggcca aacctgtcac ccagatcgtc agcgccgagg cctggggtag agcagactgt   1680

ggcttcacct ccgagtctta ccagcaaggg gtcctgtctg ccaccatcct ctatgagatc   1740

ttgctaggga aggccacctt gtatgccgtg ctggtcagtg ccctcgtgct gatggccatg   1800

gtcaagagaa aggattccag aggctagtct aga                                1833
```

<210> SEQ ID NO 36
<211> LENGTH: 1833
<212> TYPE: DNA
<213> ORGANISM: Homo sapiens

<400> SEQUENCE: 36

```
ggatccgcca ccatgaaatc cttgagagtt ttactagtga tcctgtggct tcagttgagc     60

tgggtttgga gccaacagaa ggaggtggag cagaattctg gacccctcag tgttccagag    120

ggagccattg cctctctcaa ctgcacttac agtgaccgag gttcccagtc cttcttctgg    180

tacagacaat attctgggaa aagccctgag ttgataatgt ccatatactc caatggtgac    240

aaagaagatg gaaggtttac agcacagctc aataaagcca gccagtatgt ttctctgctc    300

atcagagact cccagcccag tgattcagcc acctacctct gtgccgtgat ctccaattca    360

ggaaacacac ctcttgtctt tggaaagggc acaagacttt ctgtgattgc aaatatccag    420

aaccctgacc ctgccgtgta ccagctgaga gactctaaat ccagtgacaa gtctgtctgc    480

ctattcaccg attttgattc tcaaacaaat gtgtcacaaa gtaaggattc tgatgtgtat    540
```

```
atcacagaca aatgtgtgct agacatgagg tctatggact tcaagagcaa cagtgctgtg    600

gcctggagca acaaatctga ctttgcatgt gcaaacgcct tcaacaacag cattattcca    660

gaagacacct tcttccccag cccagaaagt tcctgtgatg tcaagctggt cgagaaaagc    720

tttgaaacag atacgaacct aaactttcaa aacctgtcag tgattgggtt ccgaatcctc    780

ctcctgaaag tggccgggtt taatctgctc atgacgctgc ggctgtggtc cagcggttcc    840

ggagccacga acttctctct gttaaagcaa gcaggagacg tggaagaaaa ccccggtccc    900

atgggctcca ggctgctctg ttgggtgctg ctttgtctcc tgggagcagg cccagtaaag    960

gctggagtca ctcaaactcc aagatatctg atcaaaacga gaggacagca agtgacactg   1020

agctgctccc ctatctctgg gcataggagt gtatcctggt accaacagac cccaggacag   1080

ggccttcagt tcctctttga atacttcagt gagacacaga gaaacaaagg aaacttccct   1140

ggtcgattct cagggcgcca gttctctaac tctcgctctg agatgaatgt gagcaccttg   1200

gagctggggg actcggccct ttatctttgc gccagcagct ttgactctga gcagtacttc   1260

gggccgggca ccaggctcac ggtcacagag gacctgaaaa acgtgttccc acccgaggtc   1320

gctgtgtttg agccatcaga agcagagatc tcccacaccc aaaaggccac actggtgtgc   1380

ctggccacag gcttctaccc cgaccacgtg gagctgagct ggtgggtgaa tgggaaggag   1440

gtgcacagtg ggtctgcac agacccgcag cccctcaagg agcagcccgc cctcaatgac   1500

tccagatact gcctgagcag ccgcctgagg gtctcggcca ccttctggca gaacccccgc   1560

aaccacttcc gctgtcaagt ccagttctac gggctctcgg agaatgacga gtggacccag   1620

gatagggcca aacctgtcac ccagatcgtc agcgccgagg cctggggtag agcagactgt   1680

ggcttcacct ccgagtctta ccagcaaggg gtcctgtctg ccaccatcct ctatgagatc   1740

ttgctaggga aggccacctt gtatgccgtg ctggtcagtg ccctcgtgct gatggccatg   1800

gtcaagagaa aggattccag aggctagtct aga                                1833
```

<210> SEQ ID NO 37
<211> LENGTH: 1836
<212> TYPE: DNA
<213> ORGANISM: Homo sapiens

<400> SEQUENCE: 37

```
ggatccgcca ccatgatgaa gagcctgcgg gtgctgctgg tgatcctgtg gctgcagctg     60

tcctgggtct ggagccagca gaaagaggtg gagcagaaca gcggccctct gagcgtgccc    120

gagggcgcca ttgccagcct gaactgcacc tacagcgacc ggggcagcca gagcttcttc    180

tggtacaggc agtacagcgg caagagcccc gagctgatca tgagcatcta cagcaacggc    240

gacaaagagg acggccggtt caccgcccag ctgaacaagg ccagccagta cgtgtctctg    300

ctgatcagag acagccagcc cagcgacagc gccacctacc tgtgcgccgt gatcagcaac    360

agcggcaaca ccccccctggt gttcggcaag ggcaccagac tgagcgtgat cgccaacatc    420

cagaaccccg accccgccgt gtaccagctg cgggacagca agagcagcga caagagcgtg    480

tgcctgttca ccgacttcga cagccagacc aacgtgagcc agagcaagga cagcgacgtg    540

tacatcaccg acaagaccgt gctggacatg cggagcatgg acttcaagag caacagcgcc    600

gtggcctggt ccaacaagag cgacttcgcc tgcgccaacg ccttcaacaa cagcatcatc    660

cccgaggaca cctttttccc cagccccgag agcagctgcg acgtgaaact ggtggagaag    720

agcttcgaga cagacaccaa cctgaacttc cagaacctgt ccgtgatcgg cttcagaatc    780

ctgctgctca aagtggctgg cttcaacctg ctgatgaccc tgcggctgtg gagcagcggg    840
```

```
tccggagcta ccaacttcag cctgctgaag caggccggcg acgtggagga aaaccctggc    900

cccatgggat ctcgcctgct gtgctgggtg ctgctgtgcc tgctgggagc cggccctgtg    960

aaggccggcg tgacccagac ccccagatac ctgatcaaga ccaggggcca gcaggtgacc   1020

ctgagctgca gccccatcag cggccacaga agcgtgagct ggtatcagca gacaccagga   1080

cagggcctgc agttcctgtt cgagtacttc agcgagacac agcggaacaa gggcaacttc   1140

cccggcaggt tcagcggcag gcagttcagc aactcccggt ccgagatgaa cgtgagcacc   1200

ctggaactgg gcgactccgc cctgtacctg tgtgccagca gcttcgacag cgagcagtac   1260

ttcggccctg gcacccggct gaccgtgacc gaggacctga agaacgtgtt cccccccgag   1320

gtggccgtgt tcgagcccag cgaggccgag atcagccaca cccagaaagc caccctggtg   1380

tgcctggcca ccggcttcta ccccgaccac gtggagctgt cttggtgggt gaacggcaaa   1440

gaggtgcaca gcggagtctc caccgacccc cagcccctga aagagcagcc cgccctgaac   1500

gacagccggt actgcctgag cagcaggctg agagtgagcg ccaccttctg gcagaacccc   1560

cggaaccact tccggtgcca ggtgcagttc tacggcctga gcgagaacga cgagtggacc   1620

caggacagag ccaagcctgt gacccagatc gtgtccgccg aggcctgggg cagagccgac   1680

tgcggcttca ccagcgagag ctatcagcag ggagtgctgt ctgccaccat cctgtacgag   1740

atcctgctgg gcaaggccac cctgtacgcc gtgctggtgt ccgccctggt gctgatggcc   1800

atggtgaagc ggaaggacag ccggggctga tctaga                             1836
```

<210> SEQ ID NO 38
<211> LENGTH: 1836
<212> TYPE: DNA
<213> ORGANISM: Homo sapiens

<400> SEQUENCE: 38

```
ggatccgcca ccatgatgaa gagcctgcgg gtgctgctgg tgatcctgtg gctgcagctg     60

tcctgggtct ggagccagca gaaagaggtg gagcagaaca gcggccctct gagcgtgccc    120

gagggcgcca ttgccagcct gaactgcacc tacagcgacc ggggcagcca gagcttcttc    180

tggtacaggc agtacagcgg caagagcccc gagctgatca tgagcatcta cagcaacggc    240

gacaaagagg acggccggtt caccgcccag ctgaacaagg ccagccagta cgtgtctctg    300

ctgatcagag acagccagcc cagcgacagc gccacctacc tgtgcgccgt gatcagcaac    360

agcggcaaca ccccccctggt gttcggcaag ggcaccagac tgagcgtgat cgccaacatc    420

cagaaccccg accccgccgt gtaccagctg cgggacagca agagcagcga caagagcgtg    480

tgcctgttca ccgacttcga cagccagacc aacgtgagcc agagcaagga cagcgacgtg    540

tacatcaccg acaagtgcgt gctggacatg cggagcatgg acttcaagag caacagcgcc    600

gtggcctggt ccaacaagag cgacttcgcc tgcgccaacg ccttcaacaa cagcatcatc    660

cccgaggaca cctttttccc cagccccgag agcagctgcg acgtgaaact ggtggagaag    720

agcttcgaga cagacaccaa cctgaacttc cagaacctgt ccgtgatcgg cttcagaatc    780

ctgctgctca aagtggctgg cttcaacctg ctgatgaccc tgcggctgtg gagcagcggg    840

tccggagcta ccaacttcag cctgctgaag caggccggcg acgtggagga aaaccctggc    900

cccatgggat ctcgcctgct gtgctgggtg ctgctgtgcc tgctgggagc cggccctgtg    960

aaggccggcg tgacccagac ccccagatac ctgatcaaga ccaggggcca gcaggtgacc   1020

ctgagctgca gccccatcag cggccacaga agcgtgagct ggtatcagca gacaccagga   1080
```

-continued

```
cagggcctgc agttcctgtt cgagtacttc agcgagacac agcggaacaa gggcaacttc   1140

cccggcaggt tcagcggcag gcagttcagc aactcccggt ccgagatgaa cgtgagcacc   1200

ctggaactgg gcgactccgc cctgtacctg tgtgccagca gcttcgacag cgagcagtac   1260

ttcggccctg gcacccggct gaccgtgacc gaggacctga agaacgtgtt cccccccgag   1320

gtggccgtgt tcgagcccag cgaggccgag atcagccaca cccagaaagc caccctggtg   1380

tgcctggcca ccggcttcta ccccgaccac gtggagctgt cttggtgggt gaacggcaaa   1440

gaggtgcaca gcggagtctg caccgacccc cagcccctga aagagcagcc cgccctgaac   1500

gacagccggt actgcctgag cagcaggctg agagtgagcg ccaccttctg gcagaacccc   1560

cggaaccact tccggtgcca ggtgcagttc tacggcctga gcgagaacga cgagtggacc   1620

caggacagag ccaagcctgt gacccagatc gtgtccgccg aggcctgggg cagagccgac   1680

tgcggcttca ccagcgagag ctatcagcag ggagtgctgt ctgccaccat cctgtacgag   1740

atcctgctgg gcaaggccac cctgtacgcc gtgctggtgt ccgccctggt gctgatggcc   1800

atggtgaagc ggaaggacag ccggggctga tctaga                             1836


<210> SEQ ID NO 39
<211> LENGTH: 9
<212> TYPE: PRT
<213> ORGANISM: Influenza virus

<400> SEQUENCE: 39

Gly Ile Leu Gly Phe Val Phe Thr Leu
1               5
```